(12) United States Patent
Alfonso San-Segundo et al.

(10) Patent No.: US 10,261,079 B2
(45) Date of Patent: Apr. 16, 2019

(54) METHOD FOR DETERMINING KINETIC PROFILES IN DRUG DISCOVERY

(71) Applicant: ENZYMLOGIC, S.L, Tres Cantos, Madrid (ES)

(72) Inventors: Ana Patricia Alfonso San-Segundo, Madrid (ES); Ana Corrionero Pérez, Madrid (ES)

(73) Assignee: ENZYMLOGIC, S.L., Tres Cantos, Madrid (ES)

( * ) Notice: Subject to any disclaimer, the term of this patent is extended or adjusted under 35 U.S.C. 154(b) by 0 days.

(21) Appl. No.: 15/760,070

(22) PCT Filed: Sep. 15, 2016

(86) PCT No.: PCT/EP2016/071901
§ 371 (c)(1),
(2) Date: Mar. 14, 2018

(87) PCT Pub. No.: WO2017/046284
PCT Pub. Date: Mar. 23, 2017

(65) Prior Publication Data
US 2019/0049441 A1    Feb. 14, 2019

(30) Foreign Application Priority Data
Sep. 16, 2015 (EP) .................................. 15185422

(51) Int. Cl.
*G01N 33/557* (2006.01)
*G01N 33/542* (2006.01)
(Continued)

(52) U.S. Cl.
CPC ........ *G01N 33/557* (2013.01); *C09K 11/7728* (2013.01); *C09K 11/7743* (2013.01);
(Continued)

(58) Field of Classification Search
None
See application file for complete search history.

(56) References Cited

U.S. PATENT DOCUMENTS
2012/0107836 A1    5/2012 Rauh et al.

FOREIGN PATENT DOCUMENTS
EP    2241619 A1    10/2010

OTHER PUBLICATIONS
International Search Report, dated Jan. 16, 2017.
(Continued)

*Primary Examiner* — Erik B Crawford
(74) *Attorney, Agent, or Firm* — Tristan A. Fuierer; Olive Law Group, PLLC

(57) ABSTRACT

The present invention relates to a reliable, robust and sensitive platform aimed to analyze the massive kinetic profile of new molecules against its main target and also against other potential targets. Thus, the present invention relates to a method for calculating the kinetic profile of a compound of interest against a target protein or polyprotein wherein it is not needed to predetermine the $K_i$ value of the compound of interest against the target protein or polyprotein before starting the assay. The present invention also discloses the use of said method in a high-throughput system for developing a Binding Kinetic Profiling assay of multiple compounds of interest against a unique target, or a Kinetic Selectivity Profiling assay of one selected compound against multiple target proteins or polyproteins to therefore establish multiple clinical profiles of potential drugs.

15 Claims, 7 Drawing Sheets

(51) Int. Cl.
  *G01N 33/50*   (2006.01)
  *G01N 33/68*   (2006.01)
  *G01N 33/533*  (2006.01)
  *C09K 11/77*   (2006.01)
  *G06F 19/18*   (2011.01)

(52) U.S. Cl.
  CPC ...... *C09K 11/7759* (2013.01); *G01N 33/5008* (2013.01); *G01N 33/533* (2013.01); *G01N 33/542* (2013.01); *G01N 33/6845* (2013.01); *G06F 19/18* (2013.01); *G01N 2500/02* (2013.01)

(56) References Cited

OTHER PUBLICATIONS

Copeland, Robert A., et al.; "Drug-target residence time and its implications for lead optimization," Nature Reviews Drug Discovery, 2006, pp. 730-739, vol. 5; doi: 10.1038/nrd2082.

Dahl, Göran, et al.; "Pharmacokinetics and the drug-target residence time concept," Drug Discovery Today, 2013, vol. 18(15-16), pp. 697-707.

Elg, Margareta, et al.; "The Importance of Enzyme Inhibition Kinetics for the Effect of Thrombin Inhibitors in a Rat Model of Arterial Thrombosis," Thromb Haemost, 1997, pp. 1286-1292, vol. 78.

Emami-Nemini, Alexander, et at.; "Time-resolved fluorescence ligand binding for G protein-coupled receptors," Nature Protocols, 2013, pp. 1307-1320, vol. 8.

Langlois, Xavier, et al.; "Pharmacology of JNJ-37822681, a Specific and Fast-Dissociating D2 Antagonist for the Treatment of Schizophrenia," The Journal of Pharmacology and Experimental Therapeutics, 2012, pp. 91-105, vol. 342.

Liedberg, BO, et al.; "Surface Plasmon Resonance for Gas Detection and Biosensing," Sensors and Actuators, 1983, pp. 299-304, vol. 4.

Motulsky, HJ, et al.; "The Kinetics of Competitive Radioligand Binding Predicted by the Law of Mass Action," Molecular Pharmacology, 1984, pp. 1-9, vol. 25.

Stoddart, Leigh A., et al.; "Fluorescence- and bioluminescence-based approaches to study GPCR ligand binding," British Journal of Pharmacology, 2015, pp. 1-10; DOI: 10.1111/bph.13316.

Swinney, David C., "The role of binding kinetics in therapeutically useful drug action," Current Opinion in Drug Discovery & Development, 2009, pp. 31-39, vol. 12.

Sykes, David A., et al., "Slow receptor dissociation is not a key factor in the duration of action of inhaled long-acting B2-adrenoceptor agonists," British Journal of Pharmacology, 2012 pp. 2672-2683, vol. 165.

Tresadern, Gary, et al.; "Molecular properties affecting fast dissociation from the D2 receptor," Bioorganic & Medicinal Chemistry, 2011, pp. 2231-2241, vol. 19.

Zhang, Rumin, et al.; "Binding kinetics and mechanism of action: toward the discovery and development of better and nest in class drugs," Expert Opinion Drug Discovery, 2010, pp. 1023-1029, vol. 5.

Corrigendum-Copeland, Robert A., et al.; "Drug-target residence time and its implications for lead optimization," Nature Reviews Drug Discovery, 2006, pp. 730-739, vol. 5; doi: 10.1038/nrd2082.

Motulsky, HJ, et al.; Correction to "The Kinetics of Competitive Radioligand Binding Predicted by the Law of Mass-Action," Molecular Pharmacology, 1984, pp. 1-9, vol. 25.

METHOD FOR DETERMINING KINETIC PROFILES IN DRUG DISCOVERY

CROSS-REFERENCE TO RELATED APPLICATIONS

This application is filed under the provisions of 35 U.S.C. § 371 and claims the priority of International Patent Application No. PCT/EP2016/071901, filed on 15 Sep. 2016 entitled "METHOD FOR DETERMINING KINETIC PROFILES IN DRUG DISCOVERY" in the name of Ana Patricia ALFONSO SAN-SEGUNDO et al., which claims priority to European Application No. 15185422.1 filed on 16 Sep. 2015, both of which are hereby incorporated by reference herein in their entirety.

TECHNICAL FIELD

The invention relates to the field of pharmaceutical area and drug discovery. It is based on the development of a high throughput platform for determining simply and rapidly the kinetic profile of new compounds in development and their potential targets in the pharmaceutical area. It is intended for use in pharmaceutical and biotech companies focused on rational drug discovery projects.

BACKGROUND

Target-based drug discovery approaches have traditionally used steady-state affinity as the main parameter to assess a compound activity and predict its performance in relevant biological models. The majority of drug discovery projects rely upon estimates of compound affinity to a target protein to guide medicinal chemistry in early stages. However, evidence is plentiful that compounds with the same affinity but very different on-($K_{on}$) and off-rates ($K_{off}$) can have a very different biological activity profile. Many experts recognize kinetic binding data as a decisive element in drug discovery that directly impact drug efficacy and safety (Copeland 2006; Swinney 2009; Mosnma 2010). For instance, compounds displaying diffusion-controlled association rates are expected to be more efficient thrombin inhibitors (Elg 1997) and transient kinetic can also be an advantage in the development of antipsychotic drugs, where mechanism-based toxicity can occur if the target receptor is inhibited for a long period of time (Tresadern 2011). On the other hand, the selectivity and efficacy of drugs with longer residence time than their plasma half-lives are likely to be underestimated by classical pharmacokinetic/pharmacodynamic models, and the inclusion of binding kinetic data is expected to really improve the predictive value of these models (Dahl 2013).

There are a variety of instruments and measurement techniques for kinetic analysis. Classical methods such as stopped flow, jump dilution and radioligand binding competition assays are tedious and cumbersome, mostly of limited throughput. There are many examples of kinetic characterization by using radiolabel ligands, most of them using radioligand competition assays and the mathematical model described by Motulski and Mahan in the eighties (Motulski 1984). To perform these assays, commonly a titrated ligand analog to the natural substrate is synthesized and custom-labeled. This radioactive ligand is first characterized kinetically to determine its association and dissociation rates. Then, unknown ligand (non-radioactive) plus the radioactive ligand are added simultaneously to the reaction mixture, and the reaction is leaved for different times. After stopping reactions, separation of bound from free radioligand is performed by rapid filtration techniques (as GF/B filter plate using a FilterMate harvester, PerkinElmer) and filters must be extensively washed before adding the scintillation cocktail. Filter-bound radioactivity is further measured by scintillation spectrometry, using conventional scintillation counters. As can be shown, these methods are tedious and time-consuming, and several incubating and washing steps are needed before the final read-out of each time point. Moreover, special care it is needed to work, store and destroy radiolabeled compounds.

Recently, some TR-FRET binding methods have been adapted to measure off-rates ($K_{off}$), reporting binding events in real time and using the classical large dilution method (LanthaScreen™_binding and Transcreener™). Nevertheless, these methods rely on previous knowledge of the affinity of the drug target interaction, which must be previously determined in classical titration experiments with different concentration of inhibitors. Then, every molecule must be pre-incubated with the target at a concentration between 10 to 40 times its $K_i$, assuring that all binding sites are occupied by the inhibitor (>90%). As the affinity of a molecule against its target is an intrinsic feature of each molecule, the affinities of different molecules vary in a broad range. To automatize this process, it is necessary to use sophisticated liquid handling systems able to pick-up different volumes from different plate positions from a first plate and subsequently dispensing those volumes in specific wells of a second plate (the so-called called "cherry-picking). Moreover, analyzing compounds with very different affinities in parallel, necessarily involve the need to make intermediate dilutions of the most potent compounds. In some cases, it may be also mandatory to use intermediate dilution plates to avoid excessive cost associated with large volumes. As it can be easily deduced, the above protocol is not useful to reach kinetic analysis in a high-throughput format. This is one of the main reasons why the kinetic profile of molecules is traditionally done only with selected molecules that have already successfully advance in the drug-discovery process (molecules that are working in an appropriate way in animal models or in clinical trials).

Other kinetic methods rely on label-free biophysical techniques, including isothermal titration calorimetry (ITC), nuclear magnetic resonance, mass spectrometry and biosensors, among others. ITC calls for large quantities of purified proteins and allows to moderate throughput despite the technical advancements. Therefore, Biosensor-based techniques, with Surface Plasmon Resonance (SPR) being the most prominent one, are the preferred techniques for kinetic characterization of drug candidates. The SPR based systems enable the detection and quantification of biological interactions in real time, without the use of labels (Lieberg 1983). Target of interest must be immobilized on the surface's chip and then, the analyte is injected through the system. The target immobilization is a critical step in the development of reliable SPR assays and although a variety of sensor surfaces are available and a broad range of techniques can be used for ligand immobilization, SPR is still restricted to membrane proteins, since these proteins are not robust enough to endure immobilization on a chip surface. Moreover, the immobilized targets are not in their native way, and some binding sites may be not accessible, eluding the binding of the ligand. In addition, SPR involves expensive laboratory equipment and demands highly trained users, which may difficult to be a general method to assess kinetic profiling in a high throughput format.

As can be outlined, there is an increasing demand for improved methods and technologies that enable accurate, cost-effective and high throughput measurements of drug-target association and dissociation rates. There is a need for a reliable, robust and sensitive platform aimed to analyze the massive kinetic profile of new molecules against its main and other potential targets.

Here we describe a robust and sensitive platform aimed to determine the massive kinetic profile of new molecules against its main target (Binding Kinetics Profiling) and also against other related targets (Kinetic Selectivity Profiling) in a high-throughput format. The platform of the invention combines the versatility of radio-ligand binding assays with the advantages of new homogeneous assays based on fluorescent probes, thus saving time and costs, and also protecting the environment.

The access to kinetic data at the early stages of the discovery process will create great opportunities for a much improved early drug discovery paradigm. In fact, such considerations have guided the first reported examples of lead compounds and clinical drug candidates selected during early stages on the basis of their target binding kinetics (Langlois 2012).

DESCRIPTION OF THE INVENTION

Brief Description of the Invention

The present invention relates to a reliable, robust and sensitive platform aimed to analyze the massive kinetic profile of new molecules against its main target (Binding Kinetics Profiling) and also against other potential targets (Kinetic Selectivity Profiling).

The present invention relates to a method for calculating the kinetic profile of a compound of interest against a target protein or polyprotein, which comprises the following steps:
  a. Mixing simultaneously in a well of a microplate:
    (i) a first molecule at a first concentration of between 1-500 nM,
    (ii) said target protein or polyprotein at a second concentration of between 0.5-50 nM, and
    (iii) a third molecule at a saturation concentration for the target protein or polyprotein of (ii),
    wherein said first molecule has affinity for said target protein or polyprotein and is labeled with a first fluorescent molecule, and said target protein or polyprotein is labeled with a second fluorescent molecule or a luciferase, or said target protein or polyprotein is bonded to between 0.5-5 nM of an antibody, wherein said antibody is labeled with a second fluorescent molecule or a luciferase,
    wherein said first fluorescent molecule is an acceptor fluorophore, said second fluorescent molecule is a donor fluorophore, and said luciferase catalyzes production of a luminescent molecule that is a donor luminophore, and
    wherein the third molecule is an inhibitor of the target protein or polyprotein which competes for the same binding sites of the target with the first molecule;
  b. Mixing simultaneously in each of n different wells of said microplate:
    (i) said first molecule at said first concentration,
    (ii) said target protein or polyprotein at said second concentration, and
    (iii) a compound of interest at a third concentration
    wherein said first molecule has affinity for said target protein or polyprotein and is labeled with said first fluorescent molecule and said target protein or polyprotein is labeled with said second fluorescent molecule or a luciferase, or said target protein or polyprotein is bonded to 0.5-5 nM of an antibody labeled with said second fluorescent molecule or a luciferase,
    wherein the third concentration is different in each of the n different wells of said microplate, wherein steps a) and b) are performed simultaneously;
  c. Measuring the emission intensity of the fluorescence signals emitted by the donor fluorophore and acceptor fluorophore or the emission intensity of the signals emitted by the donor luminophore and acceptor fluorophore in each mixture obtained in steps a) and b) with a microplate reader at specific points in time from 0 up to 15 hours, wherein said emission intensities are simultaneously measured for all wells of said microplate at each specific point in time;
  d. Calculating the corrected emission ratio (ER*) for each of the n different mixtures obtained in step b) at each specific point in time, wherein the corrected emission ratio for a given mixture obtained in step b) at a given specific point in time, is calculated by subtracting the emission ratio of the mixture obtained in step a) at said given specific point in time ($ER_a$) from the emission ratio of said mixture obtained in step b) at said given specific point in time ($ER_b$),
    wherein:
    $ER_a$ is calculated by dividing the acceptor fluorophore emission intensity in said mixture obtained in step a) at said given specific point in time ($afEI_a$) by the donor fluorophore or donor luminophore emission intensity in said mixture obtained in step a) at said given specific point in time ($dfEI_a$), and
    $ER_b$ is calculated by dividing the acceptor fluorophore emission intensity in said mixture obtained in step b) at said given specific point in time ($afEI_b$) by the donor fluorophore or donor luminophore emission intensity in said mixture obtained in step b) at said given specific point in time ($dfEI_b$); and
  e. Calculating the kinetic profile of each compound of interest against a target protein or polyprotein from the corrected emission ratios (ER*) obtained in step d) by fitting said corrected emission ratios (ER*) to a kinetic competitive binding model, wherein the kinetic profile of said compound of interest against said target protein or polyprotein is defined by: the affinity constant ($K_d$), the association rate constant ($k_{on}$), the dissociation rate constant ($k_{off}$) and the residence time ($t_{1/2}$) of said compound of interest against said target protein or polyprotein,
  with the proviso that the value of the inhibitor constant ($K_i$) of the compound of interest against the target protein or polyprotein does not need to be predetermined.

The present invention also relates to a method for calculating the kinetic profile of a compound of interest against a target protein or polyprotein, which comprises the following steps:
  a. Mixing simultaneously in a well of a microplate:
    (i) a first molecule at a first concentration of between 1-500 nM,
    (ii) said target protein or polyprotein at a second concentration of between 0.5-50 nM, and
    (iii) a third molecule at a saturation concentration for the target protein or polyprotein of (ii), wherein said first molecule has affinity for said target protein or polyprotein and is labeled with a first fluorescent molecule, and said target protein or polyprotein is labeled with a second fluorescent molecule or a luciferase, or said target protein or polyprotein is bonded to between 0.5-5 nM of an antibody, wherein said antibody is labeled with a second fluorescent molecule or a luciferase, wherein said first fluorescent molecule is an acceptor fluorophore, said second fluorescent molecule is a donor fluorophore, and said luciferase catalyzes production of a luminescent molecule that is a donor luminophore, and wherein the third molecule is an inhibitor of the target protein or polyprotein which competes for the same binding sites of the target with the first molecule;

b. Mixing simultaneously in each of n different wells of said microplate:
  (i) said first molecule at said first concentration,
  (ii) said target protein or polyprotein at said second concentration, and
  (iii) a compound of interest at a third concentration
  wherein said first molecule has affinity for said target protein or polyprotein and is labeled with said first fluorescent molecule and said target protein or polyprotein is labeled with said second fluorescent molecule or a luciferase, or said target protein or polyprotein is bonded to 0.5-5 nM of an antibody labeled with said second fluorescent molecule or a luciferase, wherein the third concentration is different in each of the n different wells of said microplate, wherein steps a) and b) are performed simultaneously;

c. Measuring the emission intensity of the fluorescence signals emitted by the donor fluorophore and acceptor fluorophore or the emission intensity of the signals emitted by the donor luminophore and acceptor fluorophore in each mixture obtained in steps a) and b) with a microplate reader at specific points in time from 0 up to 15 hours, wherein said emission intensities are measured for all wells of said microplate at within five minutes of each specific point in time;

d. Calculating the corrected emission ratio (ER*) for each of the n different mixtures obtained in step b) at each specific point in time, wherein the corrected emission ratio for a given mixture obtained in step b) at a given specific point in time, is calculated by subtracting the emission ratio of the mixture obtained in step a) at said given specific point in time ($ER_a$) from the emission ratio of said mixture obtained in step b) at said given specific point in time ($ER_b$), wherein:
  $ER_a$ is calculated by dividing the acceptor fluorophore emission intensity in said mixture obtained in step a) at said given specific point in time ($afEI_a$) by the donor fluorophore or donor luminophore emission intensity in said mixture obtained in step a) at said given specific point in time ($dfEI_a$), and $ER_b$ is calculated by dividing the acceptor fluorophore emission intensity in said mixture obtained in step b) at said given specific point in time ($afEI_b$) by the donor fluorophore or donor luminophore emission intensity in said mixture obtained in step b) at said given specific point in time ($dfEI_b$); and e. Calculating the kinetic profile of each compound of interest against a target protein or polyprotein from the corrected emission ratios (ER*) obtained in step d) by fitting said corrected emission ratios (ER*) to a kinetic competitive binding model, wherein the kinetic profile of said compound of interest against said target protein or polyprotein is defined by: the affinity constant ($K_d$), the association rate constant ($k_{on}$), the dissociation rate constant ($k_{off}$) and the residence time ($t_{1/2}$) of said compound of interest against said target protein or polyprotein, with the proviso that the value of the inhibitor constant ($K_i$) of the compound of interest against the target protein or polyprotein does not need to be predetermined, and with the proviso that the emission intensities are not simultaneously measured for all wells of said microplate at each specific point in time.

DETAILED DESCRIPTION OF THE INVENTION

Figure 1:
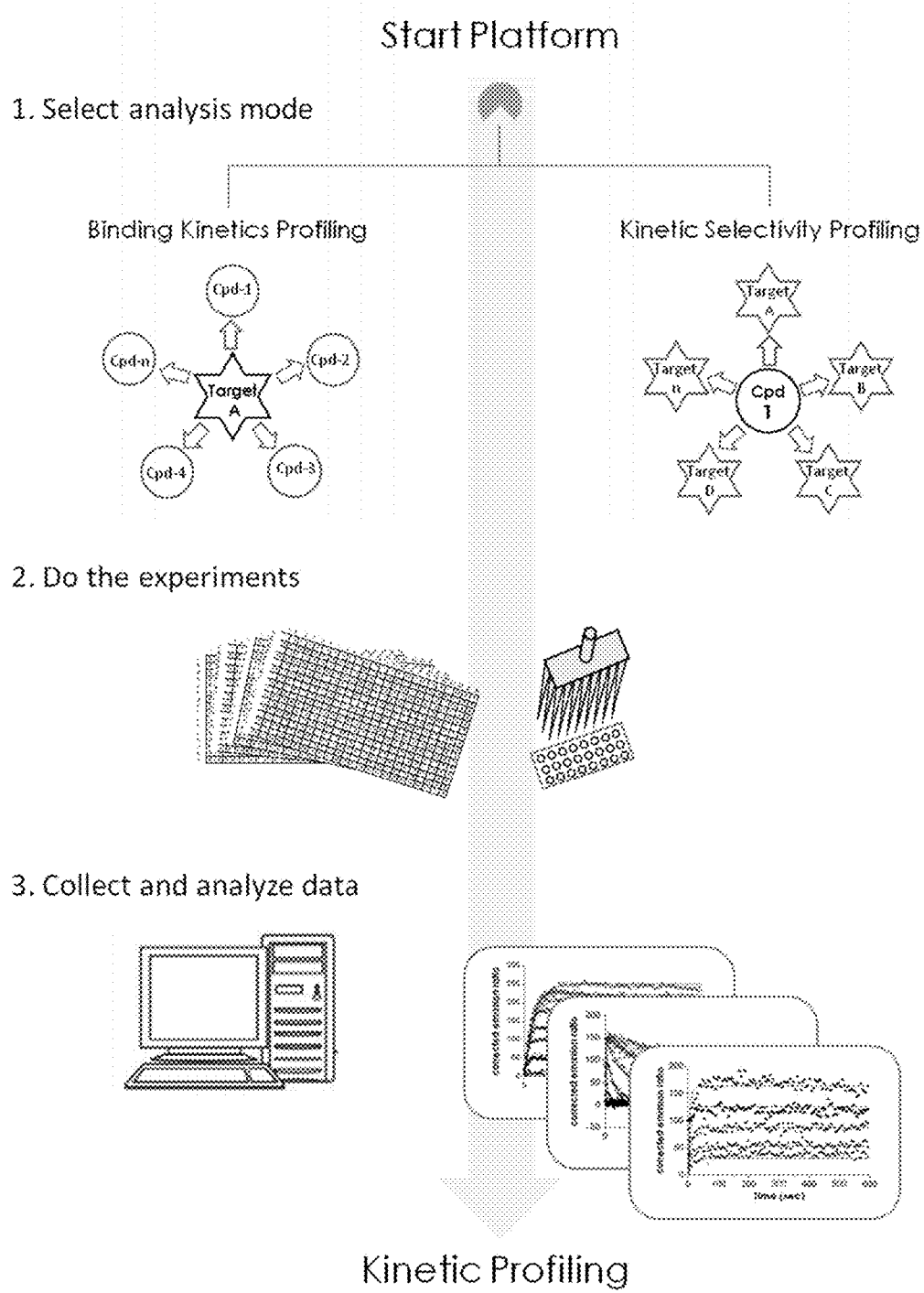
FIG. 1: Workflow scheme of the platform. After choosing the analysis mode (Binding Kinetic Profiling or Selectivity Kinetic Profiling), the assays are performed in the microplate and the emitted fluorescence is acquired by the microplate reader. The data recorded by the microplate reader are managed by the Kinetic data Management E.0 software application and the determination of the kinetic profiling of each compound is obtained.

The present invention relates to a reliable, robust and sensitive platform aimed to analyze the kinetic profiles en masse of new molecules or compounds of interest against their main target proteins or polyproteins and against potential such target proteins or polyproteins. The method is for calculating the kinetic profile of a compound of interest against a target protein or polyprotein, which comprises the following steps:

a. Mixing simultaneously in a well of a microplate:
  (i) a first molecule at a first concentration of between 1-500 nM,
  (ii) said target protein or polyprotein at a second concentration of between 0.5-50 nM, and
  (iii) a third molecule at a saturation concentration for the target protein or polyprotein of (ii),
  wherein said first molecule has affinity for said target protein or polyprotein and is labeled with a first fluorescent molecule, and said target protein or polyprotein is bonded to between 0.5-5 nM of an antibody, wherein said antibody is labeled with a second fluorescent molecule,
  wherein said first fluorescent molecule is an acceptor fluorophore and said second fluorescent molecule is a donor fluorophore, and
  wherein the third molecule is an inhibitor of the target protein or polyprotein which competes for the same binding sites of the target with the first molecule;

b. Mixing simultaneously in each of n different wells of said microplate:
  (i) said first molecule at said first concentration,
  (ii) said target protein or polyprotein at said second concentration, and
  (iii) a compound of interest at a third concentration
  wherein said first molecule has affinity for said target protein or polyprotein and is labeled with said first fluorescent molecule and said target protein or polyprotein is bonded to 0.5-5 nM of an antibody labeled with said second fluorescent molecule, wherein the third concentration is different in each of the n different wells of said microplate, wherein steps a) and b) are performed simultaneously;

c. Measuring the emission intensity of the fluorescence signals emitted by the donor fluorophore and acceptor fluorophore in each mixture obtained in steps a) and b) with a microplate reader at specific points in time from 0 up to 15 hours, wherein said emission intensities are simultaneously measured for all wells of said microplate at each specific point in time;

d. Calculating the corrected emission ratio (ER*) for each of the n different mixtures obtained in step b) at each specific point in time, wherein the corrected emission ratio for a given mixture obtained in step b) at a given specific point in time, is calculated by subtracting the emission ratio of the mixture obtained in step a) at said given specific point in time ($ER_a$) from the emission ratio of said mixture obtained in step b) at said given specific point in time ($ER_b$), wherein:
  $ER_a$ is calculated by dividing the acceptor fluorophore emission intensity in said mixture obtained in step a) at said given specific point in time ($afEI_a$) by the donor fluorophore emission intensity in said mixture obtained in step a) at said given specific point in time ($dfEI_a$), and
  $ER_b$ is calculated by dividing the acceptor fluorophore emission intensity in said mixture obtained in step b) at said given specific point in time ($afEI_b$) by the donor fluorophore emission intensity in said mixture obtained in step b) at said given specific point in time ($dfEI_b$); and e. Calculating the kinetic profile of each compound of interest against a target protein or polyprotein from the corrected emission ratios (ER*) obtained in step d) by fitting said corrected emission ratios (ER*) to a kinetic competitive binding model, wherein the kinetic profile of said compound of interest against said target protein or polyprotein is defined by: the affinity constant ($K_d$), the association rate constant ($k_{on}$), the dissociation rate constant ($k_{off}$) and the residence time ($t_{1/2}$) of said compound of interest against said target protein or polyprotein, with the proviso that the value of the inhibitor constant ($K_i$) of the compound of interest against the target protein or polyprotein does not need to be predetermined.

Alternatively, the method comprises the following steps:
a. Mixing simultaneously in a well of a microplate:
  (i) a first molecule at a first concentration of between 1-500 nM,
  (ii) said target protein or polyprotein at a second concentration of between 0.5-50 nM, and
  (iii) a third molecule at a saturation concentration for the target protein or polyprotein of (ii),
  wherein said first molecule has affinity for said target protein or polyprotein and is labeled with a first fluorescent molecule, and said target protein or polyprotein is labeled with a second fluorescent molecule or a luciferase, or said target protein or polyprotein is bonded to between 0.5-5 nM of an antibody, wherein said antibody is labeled with a second fluorescent molecule or a luciferase, wherein said first fluorescent molecule is an acceptor fluorophore, said second fluorescent molecule is a donor fluorophore, and said luciferase catalyzes production of a luminescent molecule that is a donor luminophore, and
  wherein the third molecule is an inhibitor of the target protein or polyprotein which competes for the same binding sites of the target with the first molecule;

b. Mixing simultaneously in each of n different wells of said microplate:
  (i) said first molecule at said first concentration,
  (ii) said target protein or polyprotein at said second concentration, and
  (iii) a compound of interest at a third concentration
  wherein said first molecule has affinity for said target protein or polyprotein and is labeled with said first fluorescent molecule and said target protein or polyprotein is labeled with said second fluorescent molecule or a luciferase, or said target protein or polyprotein is bonded to 0.5-5 nM of an antibody labeled with said second fluorescent molecule or a luciferase, wherein the third concentration is different in each of the n different wells of said microplate, wherein steps a) and b) are performed simultaneously;

c. Measuring the emission intensity of the fluorescence signals emitted by the donor fluorophore and acceptor fluorophore or the emission intensity of the signals emitted by the donor luminophore and acceptor fluorophore in each mixture obtained in steps a) and b) with a microplate reader at specific points in time from 0 up to 15 hours, wherein said emission intensities are measured for all wells of said microplate at within five minutes of each specific point in time;

d. Calculating the corrected emission ratio (ER*) for each of the n different mixtures obtained in step b) at each specific point in time, wherein the corrected emission ratio for a given mixture obtained in step b) at a given specific point in time, is calculated by subtracting the emission ratio of the mixture obtained in step a) at said given specific point in time ($ER_a$) from the emission ratio of said mixture obtained in step b) at said given specific point in time ($ER_b$), wherein:

$ER_a$ is calculated by dividing the acceptor fluorophore emission intensity in said mixture obtained in step a) at said given specific point in time ($afEI_a$) by the donor fluorophore or donor luminophore emission intensity in said mixture obtained in step a) at said given specific point in time ($dfEI_a$), and $ER_b$ is calculated by dividing the acceptor fluorophore emission intensity in said mixture obtained in step b) at said given specific point in time ($afEI_b$) by the donor fluorophore or donor luminophore emission intensity in said mixture obtained in step b) at said given specific point in time ($dfEI_b$); and e. Calculating the kinetic profile of each compound of interest against a target protein or polyprotein from the corrected emission ratios (ER*) obtained in step d) by fitting said corrected emission ratios (ER*) to a kinetic competitive binding model, wherein the kinetic profile of said compound of interest against said target protein or polyprotein is defined by: the affinity constant ($K_d$), the association rate constant ($k_{on}$), the dissociation rate constant ($k_{off}$) and the residence time ($t_{1/2}$) of said compound of interest against said target protein or polyprotein, with the proviso that the value of the inhibitor constant ($K_i$) of the compound of interest against the target protein or polyprotein does not need to be predetermined, and with the proviso that when the target protein or polyprotein is bonded to between 0.5-5 nM of an antibody, wherein said antibody is labeled with a second fluorescent molecule, the emission intensities are not simultaneously measured for all wells of said microplate at each specific point in time.

The object of the invention is to provide a method for determining kinetic profiles of new molecules or compounds of interest against potential targets proteins or polyproteins by a competitive binding assay.

In a preferred embodiment of the invention, the method is performed using a High Throughput System (HTS). In the present invention, a High throughput system (HTS) refers to an automated method which uses robotics, data processing and control software, liquid handling devices, and sensitive detectors, to quickly conduct millions of chemical, genetic, or pharmacological tests.

For the purpose of the present invention, the term "comprise" or "comprising", throughout the present patent description, includes, specifically, the term "consisting" or "consisting of", when referred to the method of determine the kinetic profiles in drug discovery.

The term "target protein or polyprotein" in the present invention comprises at least one enzyme, G protein-coupled receptor, ion channel, hormone receptor, structural protein and/or membrane transport protein For the present invention, the terms "compound of interest", and "first molecule" each refer to any molecule able to bind to the specific binding sites in the target protein or polyprotein to which the third molecule also binds, such as inhibitors, agonists, antagonists, drugs, effectors, metabolites among others.

An "antibody" in the present invention refers to an antibody which recognizes the target protein or polyprotein of the assay. This antibody is tagged with a donor fluorophore or a luciferase which catalyzes production of a luminescent molecule that is a donor luminophore. In a preferred embodiment, the donor fluorophore comprises a lanthanide selected from: Europium (Eu), Samarium (Sm), Terbium (Tb) or Dysprosium (Dy). In an alternative preferred embodiment, the luciferase is a luciferase having at least 80% sequence identity with a luciferase selected from the genus *Photinus* (such as firefly luciferase derived from *Photinus pyralis*), *Vibrio*, *Renilla* (such as *renilla* or RLuc luciferase derived from *Renilla reniformis*), *Metridia*, *Photorhabdus*, *Oplophorus* (such as NanoLuc® luciferase (Promega) derived from *Oplophorus gracilirostris*) or from dinoflagellates. In a more preferred embodiment, the donor fluorophore comprises a lanthanide selected from: Europium (Eu) or Terbium (Tb). In an alternative more preferred embodiment, the luciferase is a luciferase having at least 90% sequence identity with a luciferase selected from the genus *Photinus* or *Oplophorus*, even more preferably at least 95% sequence identity with a luciferase from *Photinus pyralis* such as firefly luciferase or *Oplophorus gracilirostris* such as NanoLuc® luciferase (Promega).

For the purposes of the present invention, the term "labeled with" means "bonded to". The method of the invention takes place in a microplate, microtitre plate, microwell plate or multiwall, a rectangular flat plate, usually disposable and made of plastic that features a grid of small, open divots called wells. In general, modern microplates for HTS have either 384, 1536, or 3456 wells.

For purposes of the present invention, a first molecule (herein also referred to as a "tracer") is a molecule labeled with a fluorophore, a fluorescent chemical compound that can emit light upon excitation, which is able to bind to the target protein or polyprotein of the assay. Said fluorophore can be selected among, without limiting, Alexa Fluor™ Dyes and BODIPY™ (Life Technnologies), DyLight™ Fluor (Thermo Scientific, Pierce), Atto and Tracy Dyes (Sigma Aldrich). FluoProbes™ (Interchim), etc. This fluorophore works as an acceptor fluorophore in the method of the invention. The binding of the tracer to the target protein or polyprotein (to which a second fluorescent molecule or a luciferase or the antibody which is labeled with a second fluorescent molecule or a luciferase is bound), results in a high degree of FRET (when a second fluorescent molecule is used) or BRET (when luciferase is used), whereas displacement of the tracer from the target protein or polyprotein with a target protein or polyprotein inhibitor (third molecule or compound of interest) results in a loss of FRET (when a second fluorescent molecule is used) or BRET (when luciferase is used).

For purposes of the present invention, the third molecule at a saturation concentration for the target protein or polyprotein refers to a molecule at a concentration wherein all receptors of the target are effectively occupied. The mixture in a well of the microplate of the first molecule ("tracer"), the target protein or polyprotein and the third molecule, will show possible unspecific binding between the target and the tracer, due to the fact that any fluorescence and/or luminescence signal detected from this mixture will be product of said unspecific binding, because all the receptors of the target are occupied by the third molecule and therefore the tracer would be bond to an unspecific binding site or receptor in the target molecule. Thus, in a preferred embodiment in each of steps a. and b. of the methods of the invention, the target protein or polyprotein is added to a composition comprising the other molecules disclosed in said respective steps, or a composition comprising the other molecules disclosed in said respective steps is added to the target protein or polyprotein, before mixing. Preferably, said mixing is conducted in steps a. and b. within 5 minutes of each other, more preferably within 1 minute of each other, even more preferably simultaneously. Accordingly, the target protein or polyprotein is the last compound added to each well of said microplate, or the first compound added to each well of said microplate before mixing, so that at the point immediately before binding is initiated (t=0), all binding sites of the target protein or polyprotein are unoccupied.

For purposes of the present invention, the compound of interest is represented by n different concentrations. An nth concentration refers to the concentration of said compound which comes from a serial dilution. A serial dilution refers to a stepwise dilution of a substance in solution, in a series of proportional amounts. In the present invention several dilutions of the compound of interest are tested for each target. In an embodiment of the invention, n is at least 3. Preferably n is a number between 4 and 8.

Microplate reader, plate reader, or microplate photometers, are instruments which are used to detect biological chemical or physical events of samples in microplates. They are widely used in research, drug discovery, bioassay validation, quality control and manufacturing processes in the pharmaceutical and biotechnological industry and academic organizations. Common detection modes for microplate assays are absorbance, fluorescence, intensity, luminescence, FRET (Fluorescence Resonance Energy Transfer), time-resolved fluorescence (TR-FRET), fluorescence polarization (FP) and Bioluminescence Resonance Energy Transfer (BRET).

The affinity of a reversible inhibitor or ligand is measured by its binding capacity for the target molecule, and this is typically quantified by measuring the dissociation constant for the target-inhibitor complex or target-ligand ($K_d$). In this particular case, the dissociation constant is sometimes referred as the inhibitor constant ($K_i$). This value can be related with the concentration of inhibitor (or ligand) which is required to decrease the maximal rate of the reaction (e.g. binding) by half ($IC_{50}$), using different equations depending on the inhibitory modality. The method of the invention is based on the kinetic competitive binding model and therefore, it is not needed to pre-incubate the target with a saturating concentration of each molecule to be analyzed before starting the assay. By eliminating this step there is no need to previously determine the $K_i$ value of each molecule in a classical dose-response experiment and all molecules are added at a several concentrations. Therefore, the method of the invention involves an important reduction in time and costs associated to the analysis, which are great advantages of interest for the pharmaceutical industry. In addition, the present invention tremendously simplifies the experimental design and easily allows full automation of the whole process.

The method disclosed in the invention establish a fast and simple method to determine the affinity constant ($K_d$), the association rate constant ($k_{on}$), the dissociation rate constant ($k_{off}$) and the residence time ($t_{1/2}$) of new compounds of interest against a target protein or polyprotein in a high throughput format to determine the kinetic profiles of said compounds in drug discovery. For the purposes of the present invention, the term affinity or dissociation constant ($K_d$) refers to the affinity between a ligand (such as a drug) and a protein (the target). The smaller the dissociation constant, the more tightly bound the ligand is, or the higher the affinity between ligand and protein. For the present invention, the terms association rate constant, $k_{on}$ or on-rate are used indistinctly and should be taken as synonyms. Analogously, the terms dissociation rate constant, $k_{off}$ or off-rate are used indistinctly. For the purposes of the present invention, the term residence time is quantified by relaxation constant ($\tau$), which is the reciprocal of the dissociation rate constant ($1/k_{off}$). For the present invention, the term $t_{1/2}$ refers to the dissociative half-life of a drug-target complex and can be defined as the relaxation time constant multiplied by 0.693 ($t_{1/2}=-\ln[0.5]/k_{off}$ or $t_{1/2}=-\ln[0.5]*\tau$). Thus, in one embodiment, the kinetic profile of said compound of interest against said target protein or polyprotein is defined by: the affinity constant ($K_d$), the association rate constant ($k_{on}$), the dissociation rate constant ($k_{off}$), and the relaxation constant ($\tau$) and the residence time ($t_{1/2}$) of said compound of interest against said target protein or polyprotein.

The method of the invention is based on fluorescent and other luminescent methods. Fluorescent and other luminescent methods have been extensively used by the pharmaceutical industry for the development of many biological assays aimed to screen compound in drug discovery projects. Many factors contribute to this fact, such as its high sensitivity and their broad dynamic range. Moreover, in contrasts to absorbance or radioactivity methods, that are quickly limited by their sensitivity when miniaturized, fluorescence signals are strictly proportional to fluorophore concentration, whatever the volume, allowing to miniaturization. In addition, the majority of fluorescent methods are homogeneous and can be run in a single step, avoiding washing and incubation phases in classical assays.

The vast majority of fluorescent and other luminescent methods existing in the state of the art, however, are driven by enzymatic or binding assays aimed at equilibrium binding measurements. Recently, there have been described some TR-FRET binding methods adapted to measure off-rates ($k_{off}$) using a classical large dilution method, but those methods cannot be used in a high throughput format. Moreover, they only allow the determination of the off-rate constant ($k_{off}$). On the contrary, the method of invention provides a detailed kinetic profile of each molecule, including the association, dissociation and affinity constants. Since the overall duration of a drug-target complex can be influenced by both, the $k_{on}$ and the $k_{off}$, the detailed kinetic information obtained by using the method of the present invention, for each molecule is crucial during the lead-design process and can significantly impact drug pharmacodynamics and safety in patients assessment of the temporal components of efficacy and target selectivity. The efficacy of a drug is related to the time the drug remains bound to the main target on which said drug will act. The toxicity of a compound could also be determined, based on its relationship with the kinetic selectivity. The present invention allows the determination of how many desirable or undesirable targets the drug is able to bind to, and for how long this bond remains.

Examples of the detection modes are fluorescence polarization (FP) and Time Resolved Fluorescence Resonance Energy Transfer (TR-FRET). Both methods enable the development of highly sensitive and homogeneous assays by using a far red tracer (fluorophore) to minimize compound interference and provide a robust readout. The method of the invention uses the TR-FRET assay as an example but it is possible to generalize to the methods for FP due to their similarity for a skilled person in the art. The FRET principle is based on the transfer of energy between two fluorophores, a donor and an acceptor. When the two entities come close enough to each other, excitation of the donor by a light source triggers an energy transfer towards the acceptor, which in turn emits specific fluorescence at a given wavelength. Molecular interactions between biomolecules can be assessed by coupling each partner with a fluorescent label and detecting the level of energy transfer. Time resolved FRET utilizes long-lived fluorophores combined with detection on a time-resolved fluorescence basis which allows for the minimization of background prompt fluorescence interferences (mainly compounds and proteins present in biological fluids or serum that are naturally fluorescent) which are short-lived compared to the long-lived labels used. In an embodiment of the invention, the emission intensity of the fluorescence signals emitted in the method of the invention is measured by fluorescence polarization (FP) or Time Resolved Fluorescence Resonance Energy Transfer (TR-FRET). In an alternative embodiment, the emission intensity of the luminescence signals emitted in the method of the invention is measured using Bioluminescence Resonance Energy Transfer (BRET) which enables the development of highly sensitive and homogeneous assays by using a blue-green tracer (luminophore produced by luciferase catalysis). In a more preferred embodiment, the intensity of the fluorescence signal is measured by Time Resolved Fluorescence Resonance Energy Transfer (TR-FRET) and the intensity of the luminescence signal is measured by Bioluminescence Resonance Energy Transfer (BRET). In a preferred embodiment of the invention, the donor fluorophore comprises a lanthanide selected from Europium (Eu), Dysprosium (Dy), Samarium (Sm) or Terbium (Tb) or comprises a luminescent molecule that is produced by luciferase-catalyzed oxidation of a luciferin. In a more preferred embodiment, said luciferin is selected from (4S)-2-(6-hydroxy-1,3-benzothiazol-2-yl)-4,5-dihydrothiazole-4-carboxylic acid, (E)-2-methyl-4-(2,6,6-trimethyl-1-cyclohex-1-yl)-1-buten-1-ol formate, 6-(4-hydroxyphenyl)-2-[(4-hydroxyphenyhmethyl]-8-(phenylmethyl)-7H-imidazo[3,2-a]pyrazin-3-one (coelenterazine), 2-[3-[2-[(2S)-butan-2-yl]-6-(1H-indol-3-yl)-3-oxo-7H-imidazo[2,1-c]pyrazin-8-yl]propyl]guanidine, 2-furanylmethyl-deoxy-coelenterazine, bacterial luciferin and dinoflagellate luciferin.

The methodology of the invention combines the high sensitivity and processivity of the TR-FRET technology with the advantages of the kinetic competitive binding approach described by Motulski and Mahan in the eighties, which has been extensively used with radioactive label ligands for kinetic analysis. As a consequence, the platform of the invention minimizes adverse environmental impacts avoiding radioactivity and maximizes economic benefits, reducing times, costs and volumes needed to perform kinetic profile characterization of new molecules.

In the method of the present invention, the microplate reader measures the emission intensity of each fluorescence signal (donor and acceptor fluorophores) or each luminescence and fluorescence signal (donor luminophore and acceptor fluorophore, respectively) at two different wavelengths (which will depend on the fluorophore or luminophore used in each assay) and generates csv files (comma-separated values, are files which stores tabular data, numbers and text, in plain-text form) with all the measurements determined. The method of the invention measures the kinetic profiles, preferably with a High throughput system (HTS) and the results are managed with the Kinetic data Management E.0 software application, a visual-basic software application developed by the inventors which import the data from csv files obtained in the microplate reader, identifying the assay in each well of the microplate according to a predefined layout. A predefined layout in the present invention refers to a specific organization of the samples in the microplate, set in the microplate reader and specifically selected prior to starting measuring the fluorescence or luminescence. The Kinetic data Management E.0 software application calculate the Emission Ratio of each well of the microplate and generate an output file with the recorded data. The expression Emission Ratio (ER) refers in the present invention to, for example, a TR-FRET or BRET emission ratio calculated by dividing the acceptor fluorescence emission by the respective donor fluorescence or donor luminescence emission of each well. Thus, in a preferred embodiment, the emission intensity of the fluorescence signal measured in step b) is performed by fluorescence polarization (FP) or by Time Resolved Fluorescence Resonance Energy Transfer (TR-FRET) or by Bioluminescence Resonance Energy Transfer (BRET), more preferably the measurement is performed by TR-FRET. In a further preferred embodiment, the microplate reader measures the emission intensity of each fluorescence signal at two wavelengths or measures the emission intensity of a fluorescence signal and a luminescence signal at different wavelengths, and generates a comma-separated value file with all the measurements determined in step a). In the present invention, the emission intensity of the fluorescence signals emitted by the donor fluorophore and acceptor fluorophore in each mixture obtained in steps a) and b) is measured with a microplate reader at specific points in time from 0 up to 15 hours, wherein said emission intensities are measured for all wells of said microplate at within five minutes of each specific point in time. Preferably, said emission intensities are measured for all wells of said microplate at within two minutes of each specific point in time, more preferably within one and a half minutes of each specific point in time.

In a preferred embodiment, the kinetic profile of a compound of interest against the target protein or polyprotein is defined in total or in part by the affinity constant ($K_d$), the association rate constant ($k_{on}$), the dissociation rate constant ($k_{off}$), the relaxation constant ($\tau$) and the residence time ($t_{1/2}$) of said compound of interest against said target protein or prolyprotein. In a more preferred embodiment of the invention, calculation of the kinetic profile of said compound of interest against said target protein or polyprotein is performed with a software application adjusted to a competitive binding model, preferably a kinetic competitive binding model.

The kinetic parameters of each compound of interest are performed with a software application adjusted to a competitive model. These kinetic parameters are determined by introducing the output file with the data generated by the Kinetic data Management E.0 software application in a software for analyzing molecular kinetics, for example GraphPad, Prism 6.0 (GraphPad Software, Inc., La Jolla Calif., USA), and adjusting the values to a "kinetic model of competitive binding". Said adjustment involves mathematically or statistically fitting the corrected Emission Ratio (ER*) data to said kinetic model of competitive binding. Preferably, said fitting involves regression of the corrected Emission Ratio (ER*) to said kinetic model of competitive binding. In a particular embodiment, all kinetic parameters ($K_d$, $k_{on}$, $k_{off}$, and $t_{1/2}$) are obtained at the same time for each ligand-target binding.

The method of the invention can be used in two different ways depending on the needs: Binding Kinetic Profiling and Selectivity Kinetic Profiling.

The first way, the Binding Kinetic Profiling allows screening multiple compounds against a unique target protein or polyprotein, obtaining the particular kinetic profile of each compound. This information is of particular interest to understand how different chemical structures interact in a different way with the target. These compounds may not be discriminated if evaluated by equilibrium binding affinity and such kinetic differences may indicate a novel protein conformation or a significant internal strain in the bound compound. This kinetic information will really drive medicinal chemist to select those molecules with better predicted efficiency. The importance of drug-target residence time (and dissociative half-life of the drug target binary-complex) is emphasized by for its potential impact on duration effect and target selectivity. Thus, in a preferred embodiment of the invention, the kinetic profiles of multiple compounds of interest are measured against one single target protein or polyprotein in a single microplate.

The second way, Kinetic Selectivity Profiling allows screening one selected compound against multiple targets proteins or polyproteins, obtaining information of how this particular molecule interact not only with its main target but also with other potential targets in a dynamic context. This information is also very valuable, since many drugs fail to reach the market due to safety issues. By using the platform in the two ways, it is possible to select those compounds with higher potential efficiency and better safety profiles. Moreover, using the platform in the Kinetic Selectivity Profiling mode you can also identify unknown targets and boost the potential of new therapeutic uses. Thus, in a preferred embodiment of the invention, the kinetic profiles of one single compound of interest against multiple target proteins or polyproteins are measured in a single microplate.

In a further aspect, this kinetic analysis can complement the classical Quantitative Structure Activity Relationship studies (QSAR) in the Structure Kinetic Relationship (SKR). This aspect is of crucial interest to select the best compounds to reach the market allowing making decisions soon and therefore selecting those compounds with higher efficiency potential and better safety profiles.

In a further aspect, the method of the invention allows the selection of compounds with a clinical profile that is important to patients: efficacy, safety, duration of action, greater tolerability, indication and therapeutic differentiation.

The method of the invention therefore, allows kinetic data to be obtained in the earlier preclinical phases of drug development, providing competitive advantage when it comes to identifying and improving novel therapeutic agents.

Another advantage of the method of the invention against the classical large dilution methods is its simplicity. The methods of the prior art are much more complicated and cannot be easily converted into a high-throughput format, as the present invention does. Indeed, global fitting of the kinetics of competitive binding model to the ER* data for any given compound of interest and target protein or polyprotein allows the affinity constant ($K_d$), the association rate constant ($k_{on}$), the dissociation rate constant ($k_{off}$), the relaxation constant ($\tau$) and the residence time ($t_{1/2}$) of said compound of interest to be output from a single method against said target protein or polyprotein, whereby multiple such kinetic profiles for multiple interactions of compounds of interest against target proteins or polyproteins may be obtained in a single method, as per the present invention.

In a further aspect, the method maintains an optimal assay window (>2) and a good Z' factor (>0.4) up to 15 hours by using target concentrations in the low nanomolar to picomolar range. This is a critical aspect to accurately determine the kinetic parameters of very potent molecules with non-classical behavior (tight-binding and/or slow-binding inhibitors). The prior art does not disclose kinetic data show such a high sensitivity and thus fail to estimate accurately the real kinetic parameters.

Another aspect of the invention relates to the target protein or polyprotein of the assay. In the present invention, the target protein or polyprotein comprises at least one enzyme, G protein-coupled receptor, ion channel, hormone receptor, structural protein and/or membrane transport protein. In a preferred embodiment, the target protein or polyprotein is selected from enzymes with kinase activity. The target protein or polyprotein concentration in the method of the invention is from 0.05-50 nM. In a preferred embodiment, the concentration of the target protein or polyprotein varies in the pico-molar range. The preferred pico-molar range of the target protein or polyprotein concentration is critical to accurately determine the kinetic parameters of very potent molecules with non-classical behavior (tight-binding and/or slow binding inhibitors).

In a more preferred embodiment, for purposes of the detection of the data obtained by the method of the invention, it is necessary that the target protein or polyprotein is labeled with a fluorescent molecule or a luciferase, or is bound to an antibody labeled with a fluorescent molecule or a luciferase. In a more preferred embodiment of the invention, the fluorescent molecule comprises a lanthanide. The concentration range of the labeled antibody in the present invention is from 0.5 to 5 nM. In a preferred embodiment, the lanthanide is selected between Europium (Eu), Samarium (Sm), Terbium (Tb) or Dysprosium (Dy). In a more preferred embodiment, the label of the target or of the antibody recognizing the target is Europium (Eu) or Terbium (Tb). Alternatively, the luciferase is a luciferase having at least 80% sequence identity with a luciferase selected from the genus *Photinus*, *Vibrio*, *Renilla*, *Metridia*, *Photorhabdus*, *Oplophorus* or from dinoflagellates.

Another aspect of the present invention relates to the compounds of interest which are able to bind to the target protein or polyprotein in the method of the invention. In the present invention, n refers to the number of tests performed in the same microplate for a compound of interest. Each test refers to a different concentration of said compound of interest. The n concentrations of the compound of interest are obtained by serial dilution from the most concentrated compound of interest. Preferably, n is at least 3 different concentrations of the compound of interest. In an even more preferred embodiment, n is a number between 4 and 8. Therefore, in said even more preferred embodiment, up to eight data from each compound of interest will be obtained (a data for each concentration of the compound of interest). The concentration range of the compound of interest to be tested against the target protein or polyprotein is from 100 femtomolar to 100 micromolar, preferably 10 picomolar to 50 micromolar.

Another aspect of the present invention relates to the first molecule, a labeled ligand, conjugated with a fluorescent dye (for purposes of the present invention also referred as "tracer") which recognizes the target protein or polyprotein of the assay. In an embodiment, this tracer is mixed simultaneously in a well of the microplate with the target protein or polyprotein and with a known ligand of the target protein or polyprotein at a saturating concentration. In a preferred embodiment in each of steps a. and b. of the methods of the invention, the target protein or polyprotein is added to a composition comprising the other molecules disclosed in said respective steps, or a composition comprising the other molecules disclosed in said respective steps is added to the target protein or polyprotein, before mixing, preferably wherein said mixing is conducted in steps a. and b. within 5 minutes of each other, more preferably within 1 minute of each other, even more preferably simultaneously. Accordingly, in steps a. and b., the target protein or polyprotein is the last compound added to each well of said microplate, or the first compound added to each well of said microplate before mixing, so that at the point immediately before binding is initiated (t=0), all binding sites of the target protein or polyprotein are unoccupied. The ligand at saturating concentration will occupy all the binding sites of the target protein or polyprotein, avoiding the tracer binding the same target protein or polyprotein. This is the negative control of the invention, due to the fact that any fluorescence signal detected from the acceptor fluorophore in this well will be the result of unspecific bond of this molecule to the target protein or polyprotein. In another embodiment, the tracer is mixed simultaneously in a well of a microplate with the target protein or polyprotein and with the compound or compounds of interest of the method. The compound or compounds of interest are not labeled. The tracer competes with the compound of interest for the same binding sites in each target molecule. For purposes of the present invention this binding competition between the compound of interest and the tracer constitutes "an assay". The kinetic constants $k_{on}$, $k_{off}$ and the concentration of the tracer of the present invention are known prior to perform each assay. In a preferred embodiment, the concentration of the tracer is in the range of 1-500 nM.

In another embodiment of the invention, the mixtures of the method of the invention can be performed, by a robotic arm without the interference of any person.

Another object of the present invention relates to the measurement of the intensity of the fluorescence and/or luminescence signals. This measurement is performed by a microplate reader from 0 up to 15 hours at real time and the maximum volume of each sample is 15 μl. For purposes of the present invention, real time refers to the measurement of the intensity refers to measures every each fixed periods of time up to e.g. 10 hours. In a more preferred embodiment, the total volume of each sample is 5-10 μl. In an embodiment of the invention 384 or 1536-well microplates can be used to perform the method of the invention. In a more preferred embodiment, 384 well plates are used. The microplate reader records the fluorescence and/or luminescence signals of each well according to the software provided by the manufacturer of the microplate reader, and it generates csv (coma separated values) files with the data of the intensity fluorescence and/or luminescence acquisition. Measuring the fluorescence and/or luminescence signal at 0 hours means that the microplate reader measures said signal immediately after adding all the components of the mixture.

Another aspect of the present invention relates to the layout of the microplate wherein the method of the invention takes place. The layout of the microplate for the method of the invention is selected in a visual basic application prior to the fluorescence and/or luminescence data acquisition by the microplate reader. The layout of the microplate defines the specific position of each assay in the microplate. The position in the microplate depends on the type of kinetic assay which will be performed within the method of the invention: Binding Kinetic Profiling or Selectivity Kinetic Profiling (FIG. 1). In an embodiment of the invention, the layout of the Binding Kinetic Profiling allows the analysis of a maximum of 46 kinetic analyses of 46 different compounds against a unique target in a 384-well microplate. In another embodiment, the layout of the Selectivity Kinetic Profiling allows the analysis of a maximum of 32 kinetic analyses of a unique compound against 32 different targets in a 384-well microplate.

Figure 2:
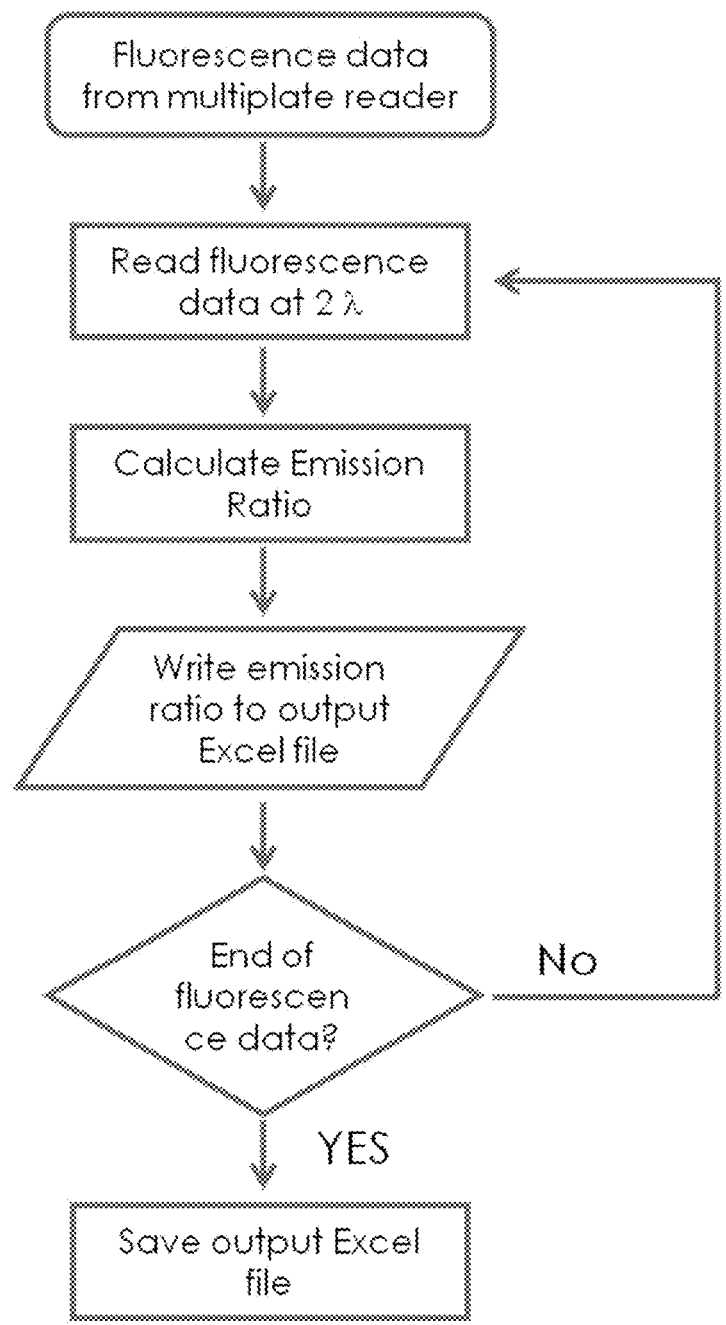
FIG. 2: Workflow scheme of the Kinetic data Management E.0 software application. The fluorescent data measurements (RFU) are obtained after reading the fluorescence of each well of the microplate at two different wavelengths. Up to 300 repeat measures per well are acquired at real time (up to 240,000 data points per microplate). The software application calculates the Emission Ratio (ER) of each well and records this value, multiplied by 10,000. When there is no more fluorescence signals, all the acquired ER data are save in an output Excel file. Depends on the predetermined layout selected in the analysis mode (Binding Kinetic Profiling or Selectivity Kinetic Profiling), different XY tables per single microplate will be obtained, wherein X is the compound concentrations in the assay, and Y is the time measurements in seconds or minutes.

Another aspect disclosed in the present invention relates to the system to manage the fluorescence and/or luminescence data acquired by the microplate reader. The fluorescence and/or luminescence data acquired by the microplate reader is managed by a software application, which imports the fluorescence and/or luminescence data from the csv files recorded by the microplate reader, to a spreadsheet output file (FIG. 2). The data obtained from the csv files before executing this software application, shows the fluorescence and/or luminescence values for each well of the plate, wherein fluorescence and/or luminescence measures are acquired every a fixed time (e.g. 6 minutes) fora determined period of time (e.g. 10 hours) at real time. Preferably emission intensities are measured for all wells of a 384-well microplate at within five minutes of each specific point in time, more preferably simultaneously. In a preferred embodiment, there are two fluorescence data from each well in each time point: the fluorescence emitted at two different wavelengths which belong to the donor molecule (the lanthanide or the antibody conjugated with the lanthanide, which binds to the target of the assay) and the fluorescence emitted by the acceptor molecule (labeled ligand). In an alternative preferred embodiment, there is one luminescence data and one fluorescence data from each well in each time point: the luminescence emitted at one wavelength by the donor molecule (the luciferase, or the antibody conjugated with the luciferase, which binds to the target of the assay) and the fluorescence emitted at another wavelength by the acceptor molecule (labeled ligand). The csv file obtained after the data acquisition by the microplate reader, is the "input file" for the software application. In a more preferred embodiment, the data presented in the input file are: "Plate number" (the number the microplate in the method), "Plate repetition" (the reading of each well at a time point), "Well" (position of the sample in the well of the microplate), "Meas Time" (time at which a measurement is acquired, from 0 minutes up to 10 hours), "Signal" (fluorescence or luminescence value), "Flashes/time" (number of readings of a fluorescence or luminescence value measured in a well). In a preferred embodiment, the readings of the fluorescence or luminescence value of each well of the microplate by the microplate reader are from 30 to 300 times at real time, more preferably 100 to 300 times at real time. In an even more preferred embodiment, up to 240.000 data per plate are obtained in less than 2 minutes in a 384-well microplate.

When the software application is executed, the Emission Ratio (ER) of each well is calculated from the input file, an ER for each assay in each time point for each compound concentration. The ER is calculated from the ratio of the fluorescence and/or luminescence data acquired from the donor and the acceptor and may be multiplied by 10.000. In the invention the specific-union data, or corrected emission ratio (ER*) is obtained for a given concentration of the compound of interest at a given time, by subtracting the ER of the negative control at said given time, defined as the wells which contain a known inhibitor (first molecule) at a saturating concentration from the ER of said compound of interest at said given concentration and said given time. The negative control allows accounting unspecific binding:

$$ER^* = afEI_b/dfEI_b - afEI_a/dfEI_a$$

Interpretation of the parameters:
$afEI_b$ refers to the intensity of the fluorescence of the acceptor fluorophore of the sample which contains the compound of interest at said given concentration and at said given time.
$dfEI_b$ refers to the intensity of the fluorescence of the donor fluorophore or donor luminophore of the sample which contains the compound of interest at said given concentration and at said given time.
$afEI_a$ refers to the intensity of the fluorescence of the acceptor fluorophore of the sample which contains the negative control at said given time.
$dfEI_a$ refers to the intensity of the fluorescence of the donor fluorophore or donor luminophore of the sample which contains the negative control at said given time.

Preferably, software is used to generate an output file (a spreadsheet) with each ER* value from the input data adjusted (fitted) to the predefined layout, in an XY table for each assay in the microplate, wherein the X values refer to the compound or unlabeled ligand concentration in the assay and the Y values refer to the time measures. In an embodiment of the invention, a maximum of 46 XY tables are generated in a Binding Kinetic Profiling assay when a 384-well microplate is used. In another embodiment, a maximum of 32 XY tables are generated in a Selectivity Kinetic Profiling assay when a 384-well microplate is used.

Another aspect disclosed in the present invention relates to the fluorescence determination method. The determination method in the invention can be performed by fluorescence polarization (FP) or time resolved Time-resolved Fluorescence Resonance Energy Transfer (TR-FRET). In a preferred embodiment, the fluorescence determination is performed by TR-FRET. Alternatively, another aspect disclosed herein relates to the luminescence determination method performed by Bioluminescence Resonance Energy Transfer (BRET).

In a preferred embodiment of the present invention the quality control acceptance criteria of the results is evaluated by statistical parameters. The negative and positive controls of the microplate are used to calculate the statistical parameters SIB and Z' factors which indicate the robustness and sensitivity of the assay performed with the method of the invention. The acceptance criteria for these factors are S/B>2 and Z'>0.4, although these factors may change depending on the target. The data acquisition in the present invention is done at a real time and consequently, those statistical parameters must be analyzed in a real time mode. It is mandatory in the invention that the Z' factor and assay window fit the established acceptance limits during the entire time of the assay, which in some cases can be extended up to 15 hours.

In a preferred embodiment of the present invention, the kinetic parameters of each compound of interest in the method of the invention are determined by fitting the data obtained from the software application to a kinetic competitive binding model. Fitting is a mathematical or statistical adjustment. Another aspect disclosed in the present invention relates to that the method of the invention does not predetermine the $K_i$ value of the target protein or polyprotein before starting the method of the invention. In a preferred embodiment, the kinetic parameters of each compound ($K_{on}$, $K_{off}$, $K_d$ and $t_{1/2}$) are calculated by a software application known for a skilled person in the art. The kinetic competitive binding model describes the kinetic behavior of two compound when compete for the binding to the same target. There is a known ligand (previously characterized kinetically, e. g. the tracer) which competes, in a real time experiment, with the compound in each assay. Data from the labeled ligand are fit to the equations described below (One-Phase association and Specific One-site binding). As the association rate of a ligand to its target molecule is dependent of ligand concentration, several concentrations were used. The progress curves are analyzed and the corresponding apparent rate constant ($k_{obs}$) are obtained. Then, $k_{obs}$ values are plotted against ligand concentration and the kinetic parameters of the label ligand are obtained by linear regression analysis. The extrapolation of the plot to the y intercept (at X=0) corresponds to the dissociation rate ($K_2$ or $K_{off}$) and the slope is equal to the association rate ($K_1$ or $K_{on}$). According to the law mass of action the ratio of $K_{off}$ to $K_{on}$ is the $K_d$ of receptor binding.

One-Phase Association $$Y = Y0 + (\text{Plateau} - Y0)*(1 - \exp(-K_{obs}*x))$$

Interpretation of the parameters:
Y0 is the Y value when X (time) is zero. It is expressed in the same units as Y,
Plateau is the Y value at infinite times, expressed in the same units as Y.
$K_{obs}$ is the apparent rate constant, expressed in reciprocal of the X axis time units. If X is in minutes, then kobs is expressed in inverse minutes.

The labeled ligand concentration and the values from the labeled ligand $K_{on}$ ($K_1$) and $K_{off}$ ($K_2$) must be introduced as "contrains" when unknown compounds are analyzed.

Specific One-Site Binding

The One-site binding describes the equilibrium binding of a ligand to a target as a function of increasing ligand concentration.

$$Y = B_{max}*X/(K_d + X)$$

Interpretation of the parameters:
Y is the specific binding.
X is the concentration of the ligand.
$B_{max}$ is the maximum number of binding sites, expressed in the same units as the Y-axis.
It is the specific binding extrapolated to very high concentrations of ligand.
$K_d$ is the equilibrium dissociation constant, expressed in the same units as the X-axis (concentration). When the ligand concentration equals $K_d$, half the binding sites are occupied at equilibrium.

In an embodiment of the invention, when the method consists on a Binding Kinetic Profiling, data are fit to the equation described below and the dissociation and association rate constants of an unlabeled compound (the compounds/ligands/new molecules of the assay) can be determined:

Kinetics of Competitive Binding $$K_A = K_1 \times L \times 10^{-9} + K_2$$

$$K_B = K_3 \times I \times 10^{-9} + K_4$$

$$S = SQRT[(K_A - K_B)^2 + 4 \times K_1 \times K_3 \times L \times I \times 10^{-18}]$$

$$K_F = 0.5 \times (K_A + K_B S)$$

$$K_S = 0.5 \times (K_A + K_B - S)$$

$$\text{DIFF} = K_F - K_S$$

$$Q = B_{max} \times K_1 \times L \times 10^{-9} / \text{DIFF}$$

$$Y = Q \times (K_4 \times \text{DIFF}/(K_F \times K_S) + [(K_4 - K_F)/K_F] \times \exp(-K_F \times X) - ((K_4 - K_S)/K_S) \times \exp(-K_S \times X)]$$

$$T = 1/K_4$$

$$t_{1/2} = \ln(2)/K_4$$

$$K_d = K_4/K_3$$

Interpretation of the parameters:

$K_A$, $K_B$, $S$, $K_F$, $K_S$, DIFF, Q and Y are mathematical groups to simplify the equations.

Constrains $K_1$ and $K_2$ are constant values of the tracer, already known prior to perform the method of the invention. These values were obtained as described above, by fitting the data to the Association kinetics equation.

$K_1$ is the association rate constant ($K_{on}$) of the labeled ligand (tracer) in $M^{-1}$ $min^{-1}$.

$K_2$ is its dissociation rate constant ($K_{off}$) of the labeled ligand (tracer) in $min^{-1}$.

L is a constant value, equal to the concentration of labeled ligand (tracer) in nM.

I is a column constant whose value comes from the column titles.

$K_3$ is the association rate constant ($K_{on}$) of unlabeled ligand (compound of interest) in $M^{-1}$ $min^-$.

$K_4$ is the dissociation rate constant ($K_{off}$) of unlabeled ligand (compound of interest) in $min^{-1}$.

$B_{max}$ is the maximum binding at equilibrium with a very high concentration of labeled-ligand expressed in the units of the Y axis, preferably in Mol. It is usually much larger than any binding seen in the experiment.

SQRT is the mathematical abbreviation for squared root.

X is time, expressed in min.

It is an object of the present invention to include several concentrations of the unknown ligands/compounds/new molecules (unlabeled) to precisely determine the kinetic parameters of the interaction with the target. Moreover, it is mandatory to fit some constrains in the model, to obtain accurate data. Thus rate constants of the first molecule or labeled ligand (tracer) must be constrained to constant values determined from previous experiments. The platform allows continuous implementation with new targets. For each particular target, a specific binding assay must be optimized and validated. In an embodiment of the invention, titration experiments with different labeled ligand (tracer) concentrations are performed and fluorescence and/or luminescence signals are monitored in a real time mode (by "continuously" obtaining data for all samples at discrete intervals over time). In a preferred embodiment, the fluorescence signals are from TR-FRET. In an alternative preferred embodiment, the bioluminescence signals are from BRET. TR-FRET data are mathematically or statistically fitted to the "Association kinetics model" and the corresponding $K_{on}$, $K_{off}$ and $K_d$ from the labeled ligand (tracer) are obtained. These values are included in the kinetic competitive model as constrain values, and influence the kinetic parameters of unknown compounds, thus it is very important to accurately determine these values.

The method disclosed in the present invention complements the classical QSAR (Quantitative Structure Activity Relationship) studies, commonly used during the lead optimization process, with relevant kinetic information data to discriminate compounds with the same affinities. As a result of medicinal chemistry rationalization, it has been stated that many compounds show extremely high potency values (pico-molar range) and thus it is necessary a highly sensitive assay to do not sub-estimate their potency. Moreover, it is necessary to discriminate among said compounds those with a different kinetic profile, i. e, those that associate/and or dissociate from the target in a different way. This aspect is of crucial interest to select those compounds with the clinical profile that is important to patients: efficacy, safety, duration of action, greater tolerability, indication and therapeutic differentiation.

Finally, the present invention combines the high sensitivity and throughput of the fluorescent and luminescent methods with the advantages of the kinetic competitive binding approach. As a consequence, this platform minimizes adverse environmental impacts avoiding radioactivity and maximizes economic benefits, reducing times and volumes needed to perform kinetic profile characterization of new molecules.

EXAMPLES

Example 1: Kinetic Characterization of a Selected Tracer for a Kinase

The present example illustrates the kinetic characterization of a selected tracer for a particular/representative kinase. The kinase of the example is the phosphoinositide 3-kinase delta, which belongs to the lipid kinase family (PI3Kinase-delta, $PI3K_{delta}$). The labeled ligand (tracer) selected is a small molecule conjugated with the fluorescent dye Alexa™ Fluor 647 (Tracer[314], Life Technologies). This molecule is an ATP-competitive analogue which binds to the $PI3K_{delta}$ and is directed by an europium labeled antibody, also bound to the kinase of the present assay. When both tracer an antibody are bound to the target of interest (e.g. $PI3K_{delta}$), there is a high TR-FRET signal, whereas displacement of the tracer with a kinase inhibitor result in a loss of TR-FRET.

The present example shows a titration experiment with different concentrations of Tracer[314]. A solution containing the enzyme $PI3K_{delta}$ (GST-p110 delta/p85 alpha, Carna Biosciences) and the europium labeled antibody LanthaScreen™ europium-labeled anti-GST goat antibody (Eu-anti GST, Life Technologies), was prepared at two times the desired concentration used in the assay (0.5 nM and 2 nM respectively). This solution was prepared in kinase buffer A (50 mM HEPES pH 7.5, 1 mM EGTA, 0.01% Brij-35, 10 mM $MgCl_2$, from Life Technologies) containing 1% DMSO. Additionally, it was prepared another solution containing a saturating concentration of a specific inhibitor of PI3Kdoifo (PI-103 at 10 micromolar) instead of DMSO in order to account the unspecific binding (low control sample or negative control).

Then, serial two fold dilutions from the tracer were prepared, ranging from 20 to 0 nanomolar. Five microliters of each solution were dispensed in 384 well plates, wherein the solution containing $PI3K_{delta}$ was added the last, once the solutions containing respectively the labeled ligand (tracer) and the inhibitor of $PI3K_{delta}$ at saturating concentration have been dispensed in the well. Immediately TR-FRET signals were collected over the time in a microplate reader (Final volume 10 µl). Measurements were carried out at room temperature, and they were repeated at intervals of 6 seconds for 10 minutes (usually this step could be extended until the binding reaches the equilibrium or the signal is stabilized).

Figure 3:
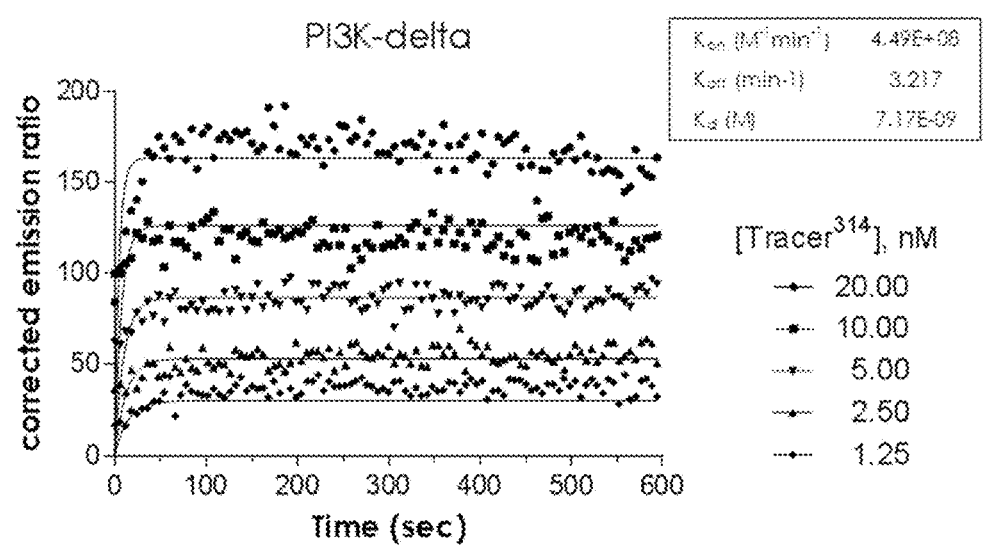
FIG. 3: Kinetic characterization of a known ligand labeled with a fluorophore (Tracer™314) against the lipid kinase PI3K-delta. Known concentrations of the tracer (0-20 nM) were tested with the target PI3K-delta. The data were fit to "One-Phase association model" and $K_{on}$, $K_{off}$ and $K_d$ from the label ligand to PI3K-delta were obtained.

The Enzymlogic Kinetic management data E.0 application is then used as explained in the detailed description of the present invention to generate a XY table plotting the corrected emission ratio (ER*) according to the different tracer concentrations (X-axis) and the time (Y-axis) (FIG. 3). These data are fit to the One-Phase association equation by using the GraphPad Prism™ software as previously described and the corresponding $K_{on}$, $K_{off}$ and $K_d$ from the labeled ligand (Tracer[314]) to PI3Kdelta are obtained. FIG. 3 includes a plot summarizing the corrected emission rate over the time at each Tracer[314] concentration (20 to 0 nM). Moreover, a table with the kinetic parameters obtained is also included summarizing the kinetic data of the Tracer[314]-PI3K$_{delta}$ interaction.

Example 2: Kinetic Characterization of Two Different Inhibitors Against the Same Target by Using the Platform in the Binding Kinetic Profiling Mode The present example illustrates the kinetic characterization of two different inhibitors against the same target by using the platform of the invention in the Binding Kinetic Profiling mode. The kinase PI3K$_{delta}$ has been selected to illustrate this example. The characterized Tracer[314] (Life Technologies) has been used as labeled ligand (tracer).

The reference compounds chosen for the present example are Wortmanine and BEZ-235 which are known for inhibiting the selected target. The affinity of these two reference compounds have been previously described by many authors at equilibrium, with $K_d$ values in the nanomolar range. Nevertheless, any kinetic parameter has been reported to date for these interactions. In order to determine the kinetic profile of these inhibitors ($K_{on}$, $K_{off}$, $K_d$ and $t_{1/2}$), experimental data were fitted to the "Kinetics of competitive binding". This model describes the kinetic behavior of two compounds when compete for the binding to the same target. There is a known ligand (Tracer[314] in this example) which competes, in a real time experiment, with the unknown compounds whose kinetic profiles we wish to know (Wortmanine and BEZ235).

Figure 4:
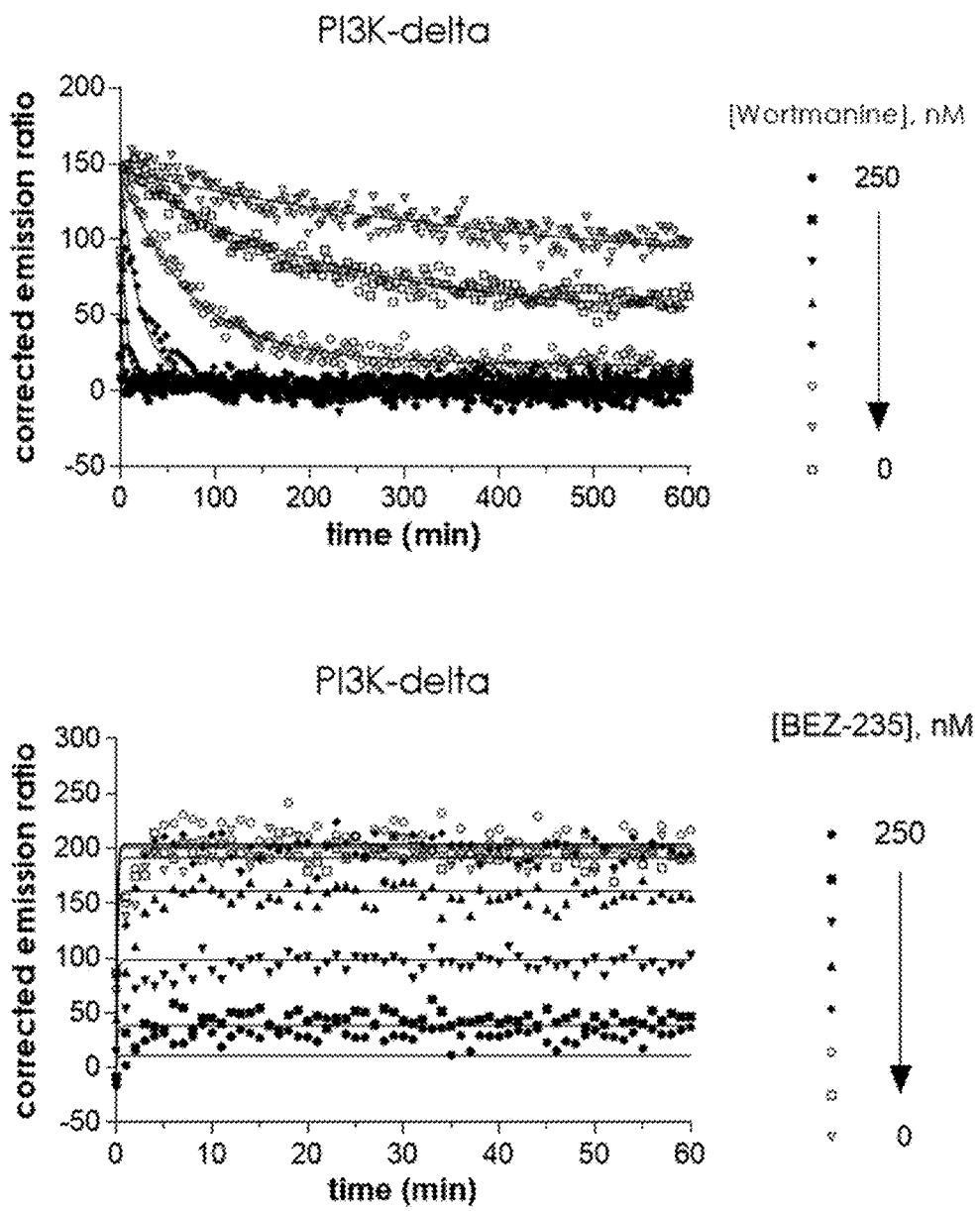
FIG. 4: Example of the Binding Kinetic Profiling. Kinetic profile characterization of two reference inhibitors against the same target (PI3K-delta). 8 concentrations of the inhibitors Wortmanine and BEZ-235 (0-250 nM) were assayed against PI3K-delta. From the corrected emission ratios (ER) obtained for each inhibitor, the $K_{on}$ ($K_3$), $K_{off}$ ($K_4$), $K_d$, τ and $t_{1/2}$ were calculated.

The experiment is performed as described in Example 1 for the tracer characterization. The samples are prepared in the kinase buffer A at the same concentrations described in example 1 (PI3K$_{delta}$ at 0.5 nM and Eu-antiGST antibody at 2 nM). Control wells in the microplate with PI-103 inhibitor at 10 µM are also included to account for unspecific binding. For the kinetic characterization of the unknown compounds, Tracer[314] is added to all wells at a constant concentration (around its $K_d$, in the present example, 5 nM) and eight different concentrations of each unknown compound (Wortmanine and BEZ235) are included in the wells of the microplate. The eight different concentrations are the result of 4-fold serial dilutions of the unknown compounds, ranging from 250 nM to 0. These serial dilutions were prepared in a mother plate (at 2 times the assay concentration) and quickly dispensed to the analysis plate, being the last one disposed in the well the kinase PI3K$_{delta}$. The TR-FRET signals corresponding to the competitive binding between the Tracer[314] and the test compounds were recorded over time as described above. The present example is illustrated in FIG. 4.

Then, the data were transformed using the Kinetic Management data E.0 software application and finally fit to the kinetic competitive model, by using the GraphPad Prism™ software. The data were fit to the equation described in the present patent application, constraining the rate constants $K_1$ ($K_{on}$) and $K_2$ ($K_{off}$) of the labeled ligand (Tracer[314]) to constant values determined from previous experiment. It is important that these analysis are performed correctly, since the kinetic parameters of the labeled ligand are included as constrains for further analysis on unknown samples within the platform.

In the present example, $K_1$ is the association rate constant of the Tracer[314] in $M^{-1}$ $min^{-1}$ (4.49E+08) and $K_2$ is its dissociation rate constant in units of $min^{-1}$ (3,217). The tracer concentration (L) is also constrained to the tracer concentration employed in the assay, i.e., 5 nM in the present example. Moreover, I is constrained to be a column constant whose value comes from the column titles. There are as many I values as different concentrations used in the experiment, expressed in nM. In this example, 8 values (i.e. 8 columns for each compound) ranging from 250 nM to 0. Then, after fitting the data to the kinetic model, the dissociation and association rate constants of the two reference compounds were determined ($K_3$ and $K_4$ respectively). In addition, $K_d$ values for each reference inhibitor can be derived from the kinetic analysis as the ratio of $K_4$ to $K_3$. The term $t_{1/2}$ is calculated as $-ln[0.5]$ divided by the $K_4$ value. The table included in FIG. 4 summarizes the kinetic parameters obtained for both PI3K$_{delta}$ inhibitors.

As can be shown in the table, Wortmanine and BEZ235 exhibit a very different kinetic profile when bound to the PI3K$_{delta}$. BEZ235 dissociate very fast from the target (mili-seconds), while the dissociative half-life estimated for the complex Wortmanine-PI3K$_{delta}$ is close to 300 min. Moreover, their affinity values are also very different, ranging from around 10 nanomolar in the case of BEZ235, to around 300 picomolar for Wortmanine.

The example described above illustrate how very different compounds can be analyzed in the same way, using the same target and compound concentrations and without the need to previously determine their $K_d$ values in classical dose-response experiments. As a consequence, the platform of the invention can be easily used in high throughput format (HTS) to kinetically characterize a broad range of molecules.

Example 3: Kinetic Characterization of Two Different Inhibitors Against Three Related Cyclin Dependent Kinases by Using the Platform in the Kinetic Selectivity Profiling Mode Example 3 illustrates how the platform of the invention works in the Kinetic Selectivity Profiling mode. This example includes two reference compounds, Sorafenib and Staurosporine, against 3 related cyclin dependent kinases (CDK7/Cyclin H MNAT1, CDK8/Cyclin C and CDK9/Cyclin T1). The same labeled molecule (tracer) is used in all the experiments (Tracer[236], Life Technologies). As described in the previous examples, the tracer used in the assay should be kinetically characterized prior to the experiment. The association ($K_{on}$), dissociation ($K_{off}$) and $K_d$ of Tracer[236] against each targeted CDK were calculated. These values were introduced as constrains for the kinetic competitive model, as explained in Example 2.

The experiments were performed similarly as described for PI3K$_{delta}$ in examples 1 and 2. The kinase concentrations used in the present example are: 2 nM for CDK8/Cyclin C and CDK9/CyclinT1 and 5 nM for CDK7/CyclinH MNAT1. The Tracer[236] concentration is 10 nM, 30 nM and 150 nM respectively for each target. An Eu-antiHis antibody was used at 2 nM in all three cases. As described previously, eight concentrations of each reference inhibitor (Sorafenib and Staurosporine) were used in every case, ranging from 1000 nM to 0 nM, result of 4-fold serial dilutions of the compounds. The TR-FRET signals corresponding to the competitive binding between the Tracer[236] and the test compounds for each target were recorded over time as described above.

Figure 5:
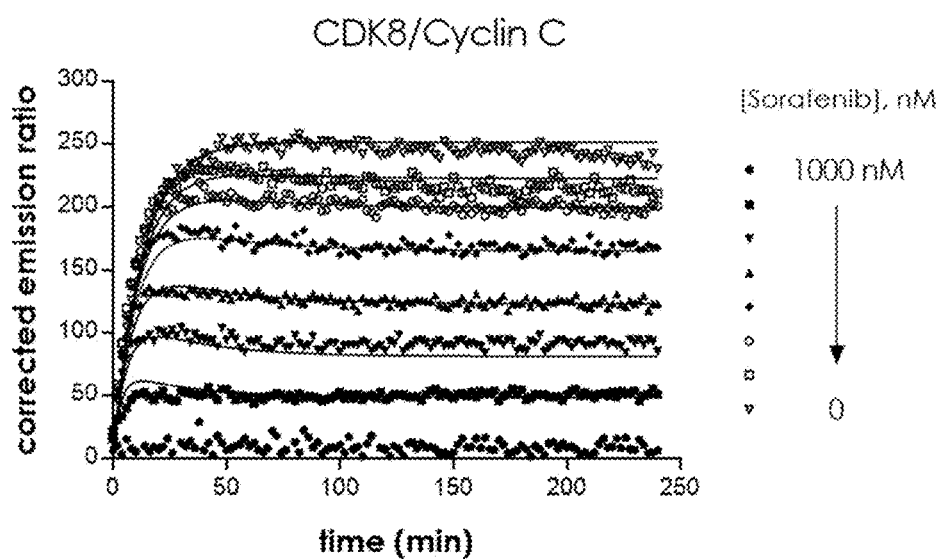
FIG. 5: Example of the Kinetic Selectivity Profiling. Kinetic profile characterization of two reference compounds against three distinct targets from the same family (transcriptional CDKs). Eight concentrations from 0 to 1000 nM of the reference compounds Sorafenib and Staurosporine were characterized against the transcriptional CDKs CDK8/Cyclin C, CDK9/Cyclin T1 and CDK7/Cyclin H/MNAT1. From the corrected emission ratios (ER) obtained for each compound against each target, the $K_{on}$ ($K_3$), $K_{off}$ ($K_4$), $K_d$, τ and $t_{1/2}$ were calculated. The values for Sorafenib against CDK9/Cyclin T1 and CDK7/Cyclin H/MNAT1 were not determined (nd).

FIG. 5 illustrate a representative plot with the corrected emission ratios (ER*) obtained from the CDK8-Sorafenib interaction over the time.

The data are transformed using the Kinetic Management data E.0 software application and finally fit to the kinetic competitive model, by using the GraphPad Prism™ software. The data were also fit to the equation described in the present patent application, constraining the rate constants $K_1$ ($K_{on}$) and $K_2$ ($K_{off}$) of the labeled ligand (Tracer[236]) to constant values determined from previous experiment. After fitting the data to the kinetic model, the dissociation and association rate constants of the two reference compounds for each target were determined as described in Example 2.

As can be shown in the table included in FIG. 5, both inhibitors show a very different profile depending on the target molecule. In one hand, Sorafenib is a specific inhibitor of CDK8/Cyclin C while Staurosporine is a pan inhibitor of the 3 CDKs, showing similar $K_d$ values for the 3 targets (between 3.2 to 8.5 nM). Interestingly, the kinetic behavior of Staurosporine is very different among the three CDKs of the example, and the interaction with CDK8 is extended for 20 min, while the interaction with CDK7 is only maintained less than 1 min.

This example illustrate how binding kinetics gives valuable information on the binding mechanism of a molecule against different targets that may influence in their potential efficacy and/or safety profile when it was used in clinical trials.

Example 4: Kinetic Characterization of a Selected Ligand of a GPCR Directly Labeled with a Fluorophore The present example illustrates the kinetic characterization of a selected ligand of a representative G protein-coupled receptor (GPCR). The GPCR of the example is the human mu-opioid receptor, which belongs to the opioid receptor family (hMOR). The labeled ligand (tracer) is a naltrexone derivative labeled with a red emitting HTRF fluorescent probe (L0005RED, Cisbio). This molecule is an opioid antagonist that binds to the hMOR. Human embryonic kidney cells (HEK) express the mu-opioid receptor directly labeled with terbium cryptate. When the tracer is bound directly to the receptor there is a high TR-FRET signal, whereas displacement of the tracer with a GPCR agonist or antagonist result in a loss of TR-FRET.

The present example shows a titration experiment with different concentrations of the opioid antagonist, ranging from 32 nM to 0 nM (serial two fold dilutions). A solution containing the HEK cells expressing the hMOR was prepared at three times the desired concentration used in the assay. Additionally, it was prepared another solution containing a saturating concentration of a specific antagonist of hMOR (Naloxone 50 micromolar, Sigma) instead of DMSO in order to account the unspecific binding (low control sample or negative control). All solutions were prepared in TAGlite buffer (LABMED, CisBio). The experiment was performed similarly to examples 1 to 3, wherein the hMOR (target) was the last one disposed in the wells.

Figure 6:
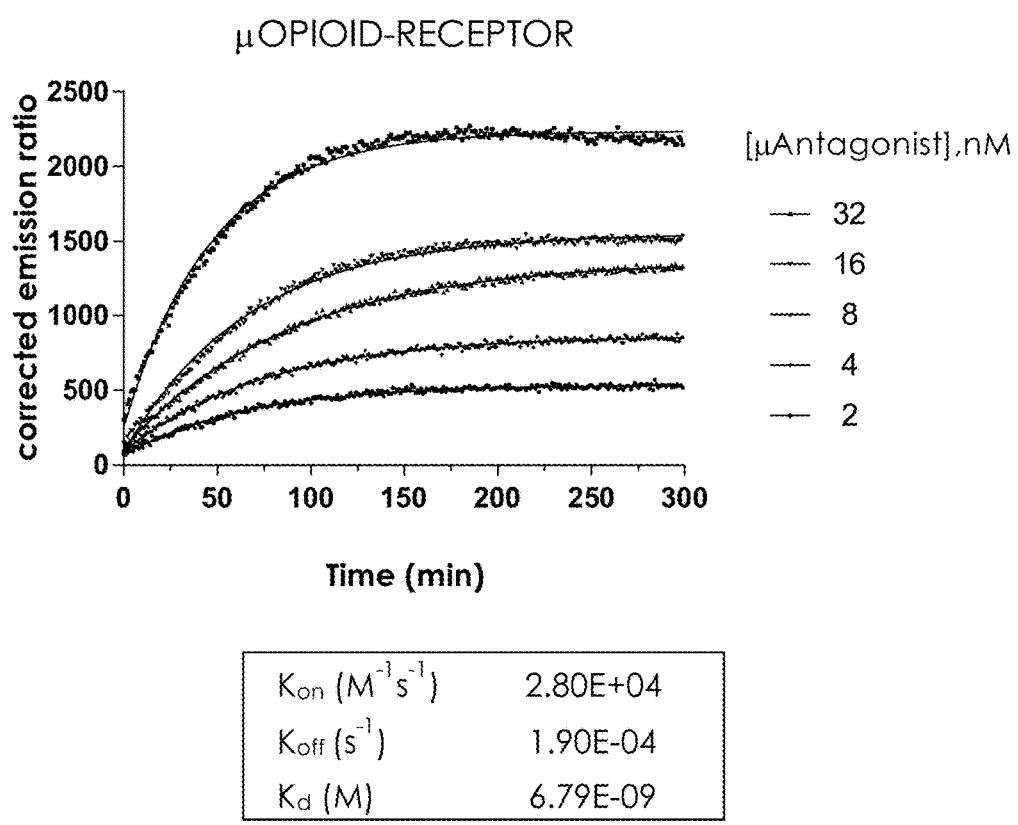
FIG. 6: Plot of the corrected emission ratio (ER*) over time according different opioid antagonist (tracer) concentrations, which, when fit to the One-Phase association equation, affords the corresponding kinetic parameters, $K_{on}$, $K_{off}$ and $K_d$, summarizing the kinetic data of the opioid antagonist L0005RED—hMOR interaction from the labeled ligand (opioid antagonist) to hMOR.

For determination of the binding kinetic constants for the Opioid antagonist, dependency of corrected emission ratio (ER*) as function of ligand concentration was measured over time in duplicate wells. The Enzymlogic Kinetic management data E.0 application is then used as explained in the detailed description of the present invention to generate a XY table plotting the corrected emission ratio (ER*) according to the different tracer concentrations (X-axis) and the time (Y-axis) (FIG. 6). These data are fit to the One-Phase association equation by using the GraphPad Prism™ software as previously described and the corresponding $k_{on}$, $k_{off}$ and $K_d$ from the labeled ligand (opioid antagonist L0005RED) to hMOR are obtained. FIG. 6 includes a plot summarizing the corrected emission rate over the time at each opioid antagonist concentration. Moreover, a table with the kinetic parameters obtained is also included summarizing the kinetic data of the opioid antagonist-hMOR interaction.

Example 5: Quality Control of the Assay

In order to establish the quality control of the platform of the invention a statistical analysis is performed automatically in every microplate. This analysis shows if the results obtained pass or not the established quality control acceptance criteria of the assay.

The negative and positive controls in the experiments are used to calculate the statistical parameters S/B and Z' factors, which indicates if an assay is robust and sensitive. Although these factors may change depending on the target, in general terms, the acceptance criteria for these factors are S/B>2 and Z'>0.4.

Figure 7:
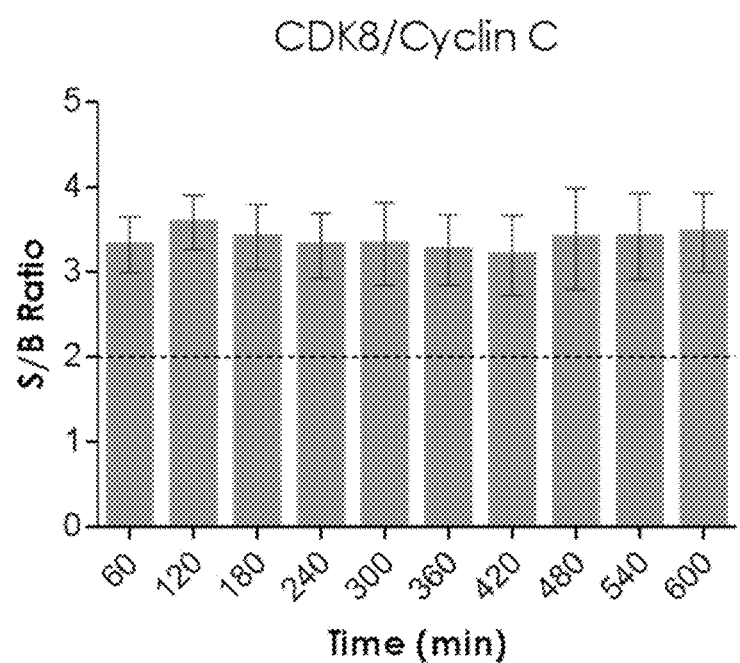
FIG. 7: Statistic parameters over the time course. Analysis to ensure that the obtained data fit to the quality control criteria. S/B Ratio and Z' value were calculated for CDK8/Cyclin C by recording fluorescence data from 0 to 600 minutes.

FIG. 7 illustrates the statistical analysis of S/B and Z' over the time course of a selected experiment performed with CDK8/Cyclin C during 10 hours. The values are calculated in a continuous mode, although are plotted at 60 minutes intervals. The experiment was performed under the same experimental conditions described in the Example 3 of this invention (2 nM CDK8/Cyclin C, 2 nM Eu-antiHis antibody and 10 nM Tracer[236]).

As can be seen in the figure, both parameters S/B ratio and Z' are well above the acceptance criteria over the whole time of the experiment.

BIBLIOGRAPHY

1. Copeland R A, Pompliano D L, Meek T D. Drug-target residence time and its implications for lead optimization. Nat Rev Discov. 2006 5(9): 730-9. Erratum in Nat Rev Drug Discov 2007 6(3): 249.
2. Swinney D C. The role of binding kinetics in therapeutically useful drug action. Curr Opin Drug Discov Devel. 2009 12(1): 31-39.
3. Zhang R, Monsma F. Binding kinetics and mechanism of action: toward the discovery and development of better and best in class drugs. Expert Opin Drug Discov. 2010 5(11):1023-9.
4. Motulski H J, Mahan L C. The kinetics of competitive radioligand binding predicted by the law of mass action. Mol Pharmacol. 1984 25(1): 1-9. Erratum in Mol Pharmacol. 2014 86(5): 592.
5. Elg M, Gustafsson D, Deinum J. The importance of enzyme inhibition kinetics for the effect of thrombin inhibitors in a rat model of arterial thrombosis. Thromb Haemost. 1997 78(4): 1286-92.

6. Tresadern G, Bartolome J M, Macdonald G J, Langlois X. Molecular properties affecting fast dissociation from the D2 receptor. Bioorg Med Chem. 2011 19(7): 2231-41.
7. Dahl G, Akerud T. Pharmacokinetics and the drug-target residence time concept. Drug Discov Today 2013 18(15-16): 697-707.
8. Lieberg B, Nylander C, Lundstrom I. Surface plasmon resonance for gas detection and biosensing. Sens. Actuators 4, 299-304 (1983).
9. Langlois X, Megens A, Lavresen H, Atack J, Cik M, to Riele P, Peeters L, Wouters R, Vermeire J, Hendrickx H, Macdonald G, De Bruyn M. Pharmacology of JNJ-37822681, a specific and fast-dissociating D2 antagonist for the treatment of schizophrenia. J Pharmacol Exp Ther. 2012 342(1):91-105.

The invention claimed is:

1. Method for calculating the kinetic profile of a compound of interest against a target protein or polyprotein, which comprises the following steps:
   a. Mixing simultaneously in a well of a microplate:
      (i) a first molecule at a first concentration of between 1-500 nM,
      (ii) said target protein or polyprotein at a second concentration of between 0.5-50 nM, and
      (iii) a third molecule at a saturation concentration for the target protein or polyprotein of (ii),
      wherein said first molecule has affinity for said target protein or polyprotein and is labeled with a first fluorescent molecule, and said target protein or polyprotein is bonded to between 0.5-5 nM of an antibody labeled with a second fluorescent molecule; or said target protein or polyprotein is labeled with said second fluorescent molecule,
      wherein said first fluorescent molecule is an acceptor fluorophore and said second fluorescent molecule is a donor fluorophore, and
      wherein the third molecule is an inhibitor of the target protein or polyprotein which competes for the same binding sites of the target with the first molecule;
   b. Mixing simultaneously in each of n different wells of said microplate:
      (i) said first molecule at said first concentration,
      (ii) said target protein or polyprotein at said second concentration, and
      (iii) a compound of interest at a third concentration
      wherein said first molecule has affinity for said target protein or polyprotein and is labeled with said first fluorescent molecule and said target protein or polyprotein is bonded to 0.5-5 nM of an antibody labeled with said second fluorescent molecule; or said target protein or polyprotein is labeled with said second fluorescent molecule,
      wherein the third concentration is different in each of the n different wells of said microplate, wherein steps a) and b) are performed simultaneously;
   c. Measuring the emission intensity of the fluorescence signals emitted by the donor fluorophore and acceptor fluorophore in each mixture obtained in steps a) and b) with a microplate reader at specific points in time from 0 up to 15 hours, wherein said emission intensities are simultaneously measured for all wells of said microplate at each specific point in time or said emission intensities are not simultaneously measured for all wells of said microplate at within five minutes of each specific point in time;
   d. Calculating the corrected emission ratio (ER*) for each of the n different mixtures obtained in step b) at each specific point in time, wherein the corrected emission ratio for a given mixture obtained in step b) at a given specific point in time, is calculated by subtracting the emission ratio of the mixture obtained in step a) at said given specific point in time ($ER_a$) from the emission ratio of said mixture obtained in step b) at said given specific point in time ($ER_b$),
      wherein:
      $ER_a$ is calculated by dividing the acceptor fluorophore emission intensity in said mixture obtained in step a) at said given specific point in time ($afEI_a$) by the donor fluorophore emission intensity in said mixture obtained in step a) at said given specific point in time ($dfEI_a$), and
      $ER_b$ is calculated by dividing the acceptor fluorophore emission intensity in said mixture obtained in step b) at said given specific point in time ($afEI_b$) by the donor fluorophore emission intensity in said mixture obtained in step b) at said given specific point in time ($dfEI_b$); and
   e. Calculating the kinetic profile of each compound of interest against a target protein or polyprotein from the corrected emission ratios (ER*) obtained in step d) by fitting said corrected emission ratios (ER*) to a kinetic competitive binding model, wherein the kinetic profile of said compound of interest against said target protein or polyprotein is defined by: the affinity constant ($K_d$), the association rate constant ($k_{on}$), the dissociation rate constant ($k_{off}$) and the residence time ($t_{1/2}$) of said compound of interest against said target protein or polyprotein,
   with the proviso that the value of the inhibitor constant ($K_i$) of the compound of interest against the target protein or polyprotein does not need to be predetermined.

2. The method according to claim 1, wherein the target protein or polyprotein is bonded to between 0.5-5 nM of an antibody labeled with a second fluorescent molecule, and wherein the emission intensities are not simultaneously measured for all wells of said microplate at each specific point in time.

3. The method according to claim 1, wherein the method for calculating the kinetic profile of each compound of interest against a target protein or polyprotein is performed in a High Throughput System (HTS).

4. The method according to claim 1, wherein the target protein or polyprotein comprises at least one enzyme, G protein-coupled receptor, ion channel, hormone receptor, structural protein and/or membrane transport protein.

5. The method according to claim 1, wherein the donor fluorophore comprises a lanthanide selected from Europium (Eu), Dysprosium (Dy), Samarium (Sm) or Terbium (Tb).

6. The method according to claim 1, wherein n is at least 3.

7. The method according to claim 6, wherein n is a number between 4 and 8.

8. The method according to claim 1, wherein the emission intensity of the fluorescence signal measured in step b) is performed by fluorescence polarization (FP) or by Time Resolved Fluorescence Resonance Energy Transfer (TR-FRET).

9. The method according to claim 8, wherein the measurement is performed by TR-FRET.

10. The method according to claim 1, wherein the microplate reader:
   a) Measures the emission intensity of each fluorescence signal at two wavelengths, and b) Generates a comma-separated value file with all the measurements determined in step a).

11. The method according to claim 1, wherein calculation of the kinetic profile of said compound of interest against said target protein or polyprotein is performed with a software application adjusted to a competitive binding model.

12. The method according to claim 1, wherein the kinetic profiles of multiple compounds of interest against one single target protein or polyprotein are measured in a single microplate.

13. The method according to claim 1, wherein the kinetic profiles of one single compound of interest against multiple target proteins or polyproteins are measured in a single microplate.

14. The method according to claim 1, wherein in each of steps a. and b. the target protein or polyprotein is added to a composition comprising the other molecules, or a composition comprising the other molecules is added to the target protein or polyprotein, before mixing.

15. The method according to claim 1, wherein the affinity constant ($K_d$), the association rate constant ($k_{on}$), the dissociation rate constant ($k_{off}$) and the residence time ($t_{1/2}$) of said compound of interest against said target protein or polyprotein are output simultaneously.

* * * * *